US012288473B2

(12) United States Patent
Singleton et al.

(10) Patent No.: US 12,288,473 B2
(45) Date of Patent: Apr. 29, 2025

(54) TECHNIQUES FOR PROVIDING INSIGHTS ACCORDING TO TAGS AND PHYSIOLOGICAL DATA

(71) Applicant: Oura Health Oy, Oulu (FI)

(72) Inventors: Alec Singleton, Toronto (CA); Johanna Leena Kyllikki Still, Oulu (FI); Dmitry Sergeev, Helsinki (FI); Janne Kukka, Santa Barbara, CA (US); Kaisa Helena Tarvainen, Oulu (FI); Miska Valkonen, Oulu (FI)

(73) Assignee: Oura Health Oy, Oulu (FI)

( * ) Notice: Subject to any disclaimer, the term of this patent is extended or adjusted under 35 U.S.C. 154(b) by 0 days.

(21) Appl. No.: 17/984,022

(22) Filed: Nov. 9, 2022

(65) Prior Publication Data

US 2023/0144761 A1    May 11, 2023

Related U.S. Application Data

(60) Provisional application No. 63/278,064, filed on Nov. 10, 2021.

(51) Int. Cl.
*G09B 19/00*    (2006.01)
*G16H 50/20*    (2018.01)

(52) U.S. Cl.
CPC ............. *G09B 19/00* (2013.01); *G16H 50/20* (2018.01)

(58) Field of Classification Search
CPC ........... G09B 19/00; G09B 5/00; G16H 50/20
See application file for complete search history.

(56) References Cited

U.S. PATENT DOCUMENTS

| 9,146,147 B1* | 9/2015 | Bakhsh ................. A47G 21/02 |
| 10,790,054 B1* | 9/2020 | Vleugels ............... A61B 5/1114 |
| 2015/0120018 A1 | 4/2015 | Wisbey et al. |
| 2015/0120311 A1* | 4/2015 | Mayer .................... G16H 40/63 705/2 |
| 2016/0026856 A1 | 1/2016 | Wisbey et al. |

(Continued)

FOREIGN PATENT DOCUMENTS

WO    WO-2022104199 A1    5/2022

OTHER PUBLICATIONS

International Search Report and Written Opinion—PCT/US2022/049463—ISA/EPO—Feb. 8, 2023.

*Primary Examiner* — Timothy A Musselman
(74) *Attorney, Agent, or Firm* — Holland & Hart LLP

(57) ABSTRACT

Methods, systems, and devices for physiological pattern recognition are described. A device may receive physiological data associated with a user from a wearable device. The device may determine that at least one physiological parameter associated with the received physiological data satisfies a physiological threshold associated with a pattern between the physiological threshold and a taggable event or a set of taggable events defined within an application associated with the wearable device. The device may then identify, based on the pattern, the taggable event or the set of taggable events indicating an activity the user engaged in that contributed to the at least one physiological parameter satisfying the physiological threshold, and cause a graphical user interface (GUI) of the device running the application to prompt the user to provide feedback associated with the identified taggable event or the identified set of taggable events.

19 Claims, 12 Drawing Sheets

(56) References Cited

U.S. PATENT DOCUMENTS

2016/0374567 A1 12/2016 Breslow et al.
2019/0076037 A1 3/2019 Bharati et al.
2020/0246543 A1* 8/2020 Sadeghzadeh ....... A61B 5/7435

* cited by examiner

TECHNIQUES FOR PROVIDING INSIGHTS ACCORDING TO TAGS AND PHYSIOLOGICAL DATA

CROSS REFERENCE

The present Application for Patent claims the benefit of U.S. Provisional Patent Application No. 63/278,064 by SINGLETON et al., entitled "TECHNIQUES FOR PROVIDING INSIGHTS ACCORDING TO TAGS AND PHYSIOLOGICAL DATA," filed Nov. 10, 2021, assigned to the assignee hereof, and expressly incorporated by reference herein.

FIELD OF TECHNOLOGY

The following relates to wearable devices and data processing, including techniques for providing insights according to tags and physiological data.

BACKGROUND

Some wearable devices may be configured to collect physiological data from a user while the user is engaged in an activity and provide insights relevant to the user. These devices may provide insights using post-activity analysis and provide insights relevant to the activity. However, these conventional techniques implemented by these devices are deficient.

DETAILED DESCRIPTION

Figure 1:
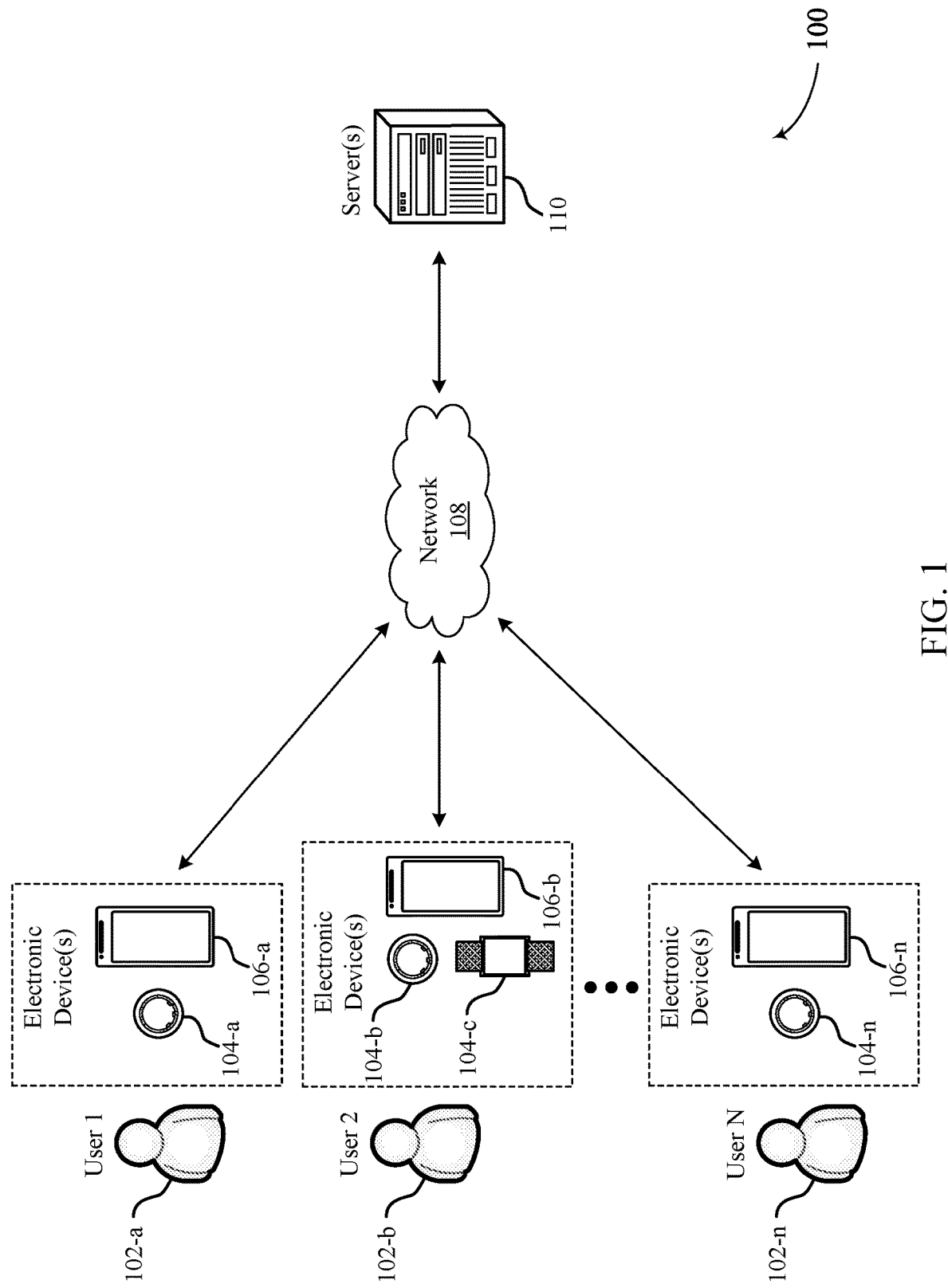
FIGS. 1 and 2 illustrate examples of systems that support techniques for providing insights according to tags and physiological data in accordance with aspects of the present disclosure.

Various applications may collect information associated with a user to provide insights or recommendations relevant to the user. An application associated with health and wellness tracking may include activity content, physiological content, and the like. For example, a wellness application may include information associated with a user's activity history, the user's physiological history relevant to the user's activity history, and the like. Existing techniques for providing insights to a user based on their activity history, physiological history, or their general preferences may fail to identify and provide insights that are most effective in causing one or more physiological responses for that particular person. For example, even though the existing techniques may provide insights about the user's general wellness in view of their activity history and physiological history, these existing techniques may fail to evaluate other metrics that may impact the user's general wellness. For example, an application associated with a wearable device may provide the functionality to a user to manually tag or otherwise input an indication of certain events, activities, or conditions (e.g., consumption of alcohol or caffeine, travel, late night meal). The tag may allow for input of events that might not be directly measured by the wearable device. However, existing techniques may not be configured to link, or may not be otherwise capable of linking, the taggable event with a physiological response or pattern of the user in a way that allows the user to understand the relationship between a taggable event and one or more physiological responses (e.g., sleep quality, mood, etc.). Furthermore, existing techniques may rely on the user to remember to manually input a tag (also referred to as a label, an indicator, a marker, a classifier, or the like) into the system that may result in far fewer taggable events being input than actually occur for a user throughout the day. As such, improvements to existing techniques of providing insights relevant to a user, especially in the context of insights related to taggable events that are intended to have a physiological, mental, or other health impact on a user, are needed.

A system including a wearable device and a user device may collect physiological data, and based on the collected physiological data, may provide insights relevant to the user. The system may be configured with a set of tags relevant to a set of taggable events that may be available to a community of users (e.g., a group of users associated with an application for a wearable device). In some implementations, the system may prompt a user to provide feedback associated with a taggable event. Additionally, the system may prompt a user to provide an indication of a tag associated with an activity the user engaged in, to increase a number of tags in the set of tags and a number of taggable events in the set of taggable events for the community of users (e.g., a group of users associated with an application for a wearable device). By increasing the number of tags and the number of taggable events, the system may improve providing insights relevant to a user, especially in the context of insights that are intended to have a physiological, mental, or other health impact on the user.

In some implementations, the system including the wearable device and the user device may collect physiological data, and based on the collected physiological data, may determine that at least one physiological parameter associated with the collected physiological data satisfies a physiological threshold associated with a pattern between the physiological threshold and a taggable event or a set of taggable events defined within an application associated with the wearable device. A pattern may be in the form of a daily report (e.g., a daily insight), a weekly report, a monthly report, or the like. In some implementations, the system may individual event-based tag insights or reports (e.g., a particular time of day, such as bedtime, or associated with a particular activity, such as exercise or meditation). The system may identify, based on the pattern, the taggable event or the plurality of taggable events indicating an activity the user engaged in that contributed to the at least one physiological parameter satisfying the physiological threshold.

A taggable event may include, but is not limited to, any activity, event, environmental condition, physiological condition, or mental condition experienced by or otherwise associated with a user, such as beverage consumption (e.g., alcoholic beverages, caffeinated beverages), food consumption, medication consumption, physical activities, illness or physical symptoms, life events, sleeping conditions, environmental factors, and the like. In some implementations, the system may cause a GUI of the user device running the application to prompt the user to provide feedback associated with the identified taggable event or the identified plurality of taggable events. For example, the system may determine (e.g., identify) and prompt a taggable event when there is a percent change to a user's Readiness Score and/or Sleep Score (e.g., a 9% positive change or a 12% negative change to the user's Readiness Score or Sleep Score) and based in part on the activity the user engaged in. Alternatively, the system may receive, via the GUI of the user device, an indication of a tag associated with the activity the user engaged in, where the tag is selected from a subset of tags displayed via the GUI with the prompt. For example, in some implementations, the system may indicate whether the user's Readiness Score or Sleep Score had a positive or negative change, and prompt the user to reflect what may have contributed to it (e.g., the activity the user engaged in). Additionally or alternatively, the system may receive via the GUI, and based on prompting the user to provide the feedback, a confirmation that the identified taggable event or the identified plurality of taggable events is related to the activity in which the user engaged.

A user may tag, via a GUI of the user device, a taggable event indicating an activity in which the user engaged (e.g., a workout, a beverage consumption, or the like). In some implementations, one or both of the tag or the taggable event may be a new tag or taggable event added by the user based on the activity in which the user engaged. The system may cause the GUI of the user device to provide feedback acknowledging one or both of the user's tag or the taggable event. The system may reward the user for providing one or both of the user's tag or the taggable event. For example, the system may cause the GUI of the user device to provide an insight that is relevant to the tag added by the user based on the activity in which the user engaged. Otherwise, the system may provide a recommendation for the user to continue adding tags in order to learn how their choices impact their general wellness.

The system may provide a respective score associated with a user's general wellness based on taggable events and physiological data. For example, a user may launch, via the user device, the application, that may display via the GUI of the user device a respective score (e.g., a Readiness Score, a Sleep Score) and insights that include physiological data and taggable events, and the contributions these data and events make to the respective scores. In some examples, a taggable event may be a late run taken by a user, and an insight may indicate that the user's late run the previous day led to a higher than average resting heart rate. Additionally, the system may provide a targeted recommendation or personalized message to the user in view of the insights. For example, in the case of the user's late run the previous day, the system may inform the user to not worry as this is a normal part of recovery. In some other examples, a taggable event may be a beverage consumption (e.g., a caffeinated beverage, an alcoholic beverage), and an insight may indicate that a user's deep sleep or REM sleep was lower than normal the previous night or that the user experienced a low sleep latency, but high resting heart rate overnight that could have been due to the beverage consumption. Additionally, the system may recommend that the user attempt to avoid certain beverages after or before a particular time in order to lessen the impact on the user's sleep quality. In some implementations, the system may support analysis on how various user choices impact users' physiology and can be derived from detecting the user's individual patterns, or from detecting patterns among a community of users, or both.

As a result, the system facilitates improvements to the user's general wellness by providing insights according to tags and the user's physiological data. While much of the present disclosure is described in the context of physiological data, this is not to be regarded as a limitation of the present disclosure. In particular, techniques described herein may enable providing insights to a user that may help improve the user's physiological data. Moreover, physiological data associated with a user may be used to update any score, measure, metric, or other abstraction associated with a user's health, mental wellness, or activity.

Aspects of the disclosure are initially described in the context of systems supporting physiological data collection from users via wearable devices. Additional aspects of the disclosure are described in the context of example GUIs. Aspects of the disclosure are further illustrated by and described with reference to apparatus diagrams, system diagrams, and flowcharts that relate to techniques for providing insights according to tags and physiological data.

FIG. 1 illustrates an example of a system 100 that supports techniques for providing insights according to tags and physiological data in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). The wearable devices 104 may also include bands, straps (e.g., flexible or inflexible bands or straps), stick-on sensors, and the like that may be positioned in other locations, such as bands around the head (e.g., a forehead headband), arm (e.g., a forearm band and/or bicep band), and/or leg (e.g., a thigh or calf band), behind the ear, under the armpit, and the like. The wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of that may measure physiological parameters and some of that may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) that emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-a associated with the first user 102-a may be communicatively coupled to the user device 106-a, where the user device 106-a is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time when a user 102 is asleep, and classify periods of time when the user 102 is asleep into one or more sleep stages (e.g., sleep stage classification). For example, as shown in FIG. 1, User 102-a may be associated with a wearable device 104-a (e.g., ring 104-a) and a user device 106-a. In this example, the ring 104-a may collect physiological data associated with the user 102-a, including temperature, heart rate, HRV, respiratory rate, and the like. In some aspects, data collected by the ring 104-a may be input to a machine learning classifier, where the machine learning classifier is configured to determine periods of time when the user 102-a is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-a via a GUI of the user device 106-a. Sleep stage classification may be used to provide feedback to a user 102-a regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-a via the wearable device 104-a. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support physiological pattern recognition. In particular, the system 100 illustrated in FIG. 1 may support techniques for providing insights to a user 102 by causing a user device 106 corresponding to the user 102 to display insights relevant to the user 102 according to tags and physiological data associated with the user 102. For example, as shown in FIG. 1, User 1 (user 102-a) may be associated with a wearable device 104-a (e.g., ring 104-a) and a user device 106-a. In this example, the ring 104-a may collect physiological data associated with the user 102-a, including heart rate, respiratory rate, skin temperature, and the like. In some examples, physiological data collected by the ring 104-a may be used to determine that at least one physiological parameter (such as a heart rate, a respiratory rate, or the like) associated with the received physiological data satisfies a physiological threshold associated with a pattern between the physiological threshold and a taggable event or a set of taggable events defined within an application associated with the wearable device 104-a (e.g., ring 104-a). The determination may be performed by any of the components of the system 100, including the ring 104-a, the user device 106-a associated with User 1, the one or more servers 110, or any combination thereof. Examples of physiological parameters may include, but are not limited to, heart rate data associated with the user 102-a, heart rate variability data associated with the user 102-a, temperature data associated with the user 102-a, respiratory rate data associated with the user 102-a, blood oxygen data associated with the user 102-a, sleep data associated with the user 102-a, readiness information associated with the user 102-a, activity data associated with the user 102-a, or the like.

Upon determining that the at least one physiological parameter associated with the received physiological data satisfies the physiological threshold associated with the pattern between the physiological threshold and the taggable event or the set of taggable events defined within the application associated with the wearable device 104-*a* (e.g., ring 104-*a*), the system 100 may identify, based on the pattern, the taggable event or the plurality of taggable events indicating an activity the user 102-*a* engaged in that contributed to the at least one physiological parameter satisfying the physiological threshold. The system 100 may cause a GUI of the user device 106-*a* running the application to prompt the user 102-*a* to provide feedback associated with the identified taggable event or the identified plurality of taggable events. The system 100 may receive, via the GUI of the user device 106-*a*, a confirmation that the identified taggable event or the identified plurality of taggable events is related to the activity in which the user 102-*a* engaged. Alternatively, the system may receive, via the GUI of the user device 106-*a*, an indication of a tag associated with the activity in which the user 102-*a* engaged. The tag may be selected by the user 102-*a* from a subset of tags displayed via the GUI with the prompt. The system 100 may thereby facilitate improvements to the user's 102 general wellness by providing insights according to tags and the user's 102 physiological data.

Any of the components of the system 100, including the ring 104-*a*, the user device 106-*a* associated with the user 102-*a*, the one or more servers 110, or any combination thereof, may determine the pattern between the physiological threshold and the taggable event or the plurality of taggable events. In some implementations, any of the components of the system 100, including the ring 104-*a*, the user device 106-*a* associated with the user 102-*a*, the one or more servers 110, or any combination thereof, may determine a set of first timestamps associated with the at least one physiological parameter (such as a heart rate, a respiratory rate, or the like) satisfying the physiological threshold and a set of second timestamps associated with a received tag. The received tag may be selected by the user 102 from the set of tags. Based on the determination, any of the components of the system 100, including the ring 104-*a*, the user device 106-*a* associated with the user 102-*a*, the one or more servers 110, or any combination thereof, may determine the pattern between the physiological threshold and the taggable event based at least in part on a temporal relationship between the set of first timestamps and the set of second timestamps.

In some implementations, any of the components of the system 100, including the ring 104-*a*, the user device 106-*a* associated with the user 102-*a*, the one or more servers 110, or any combination thereof, may determine a temporal difference between the set of first timestamps and the set of second timestamps, and determine that the temporal difference between the set of first timestamps and the set of second timestamps satisfies a correlation threshold. As a result, any of the components of the system 100, including the ring 104-*a*, the user device 106-*a* associated with the user 102-*a*, the one or more servers 110, or any combination thereof, may determine the pattern between the physiological threshold and the taggable event or the plurality of taggable events based on determining that the temporal difference between the set of first timestamps and the set of second timestamps satisfies the correlation threshold.

In some other implementations, any of the components of the system 100, including the ring 104-*a*, the user device 106-*a* associated with the user 102-*a*, the one or more servers 110, or any combination thereof, may determine the pattern between the physiological threshold and the taggable event or the plurality of taggable events by inputting one or more respective physiological parameters associated with respective physiological data collected previously from the wearable device 104-*a* and one or more respective tags of the set of tags selected previously by the user 102-*a* into a machine learning model. The machine learning model may be trained to identify temporal relationships between the respective physiological parameters and each respective tag of the one or more respective tags of the set of tags selected previously by the user 102-*a*. Any of the components of the system 100, including the ring 104-*a*, the user device 106-*a* associated with the user 102-*a*, the one or more servers 110, or any combination thereof, may update the pattern between the physiological threshold and the taggable event or the plurality of taggable events based on inputting subsequently received physiological data from the wearable device 106-*a* or the subsequently received tags associated with the activity in which the user 102-*a* engaged into the machine learning model.

In other implementations, any of the components of the system 100, including the ring 104-*a*, the user device 106-*a* associated with the user 102-*a*, the one or more servers 110, or any combination thereof, may determine the pattern between the physiological threshold and the taggable event or the plurality of taggable events by inputting one or more respective physiological parameters associated with respective physiological data collected previously from a set of users 102 (a community of users (e.g., a group of users associated with an application for a wearable device)) and one or more respective tags of the set of tags selected previously by the set of users 102 into a machine learning model. Any of the components of the system 100, including the ring 104-*a*, the user device 106-*a* associated with the user 102-*a*, the one or more servers 110, or any combination thereof, may determine the pattern between the physiological threshold and the taggable event or the plurality of taggable events based on inputting the one or more respective physiological parameters and the one or more respective tags of the set of tags selected previously by the set of users 102 into the machine learning model.

As part of providing insights according to tags and physiological data, any of the components of the system 100, including the ring 104-*a*, the user device 106-*a* associated with the user 102-*a*, the one or more servers 110, or any combination thereof, may also determine a baseline value of the at least one physiological parameter associated with the received physiological data, and determine the pattern between the physiological threshold and the taggable event or the plurality of taggable events based at least in part on the baseline value of the at least one physiological parameter associated with the received physiological data.

In some implementations, any of the components of the system 100, including the ring 104-*a*, the user device 106-*a* associated with the user 102-*a*, the one or more servers 110, or any combination thereof, may track a set of Scores (e.g., a Readiness Score, a Sleep Score, and the like) by monitoring one or more activities the user 102-*a* engaged in and one or more identified tags provided to or selected by the user 102-*a* that contribute to the set of Scores throughout a time interval (e.g., a day, a week, a month, a year, or the like). Any of the components of the system 100, including the ring 104-*a*, the user device 106-*a* associated with the user 102-*a*, the one or more servers 110, or any combination thereof, may update the Readiness Score based on tracking the Readiness Score throughout the time interval, and cause the GUI of the user device 106-*a* to output content (e.g., insights about the taggable event and physiological parameter associated with the user 102-*a*) based on updating the Readiness Score. In some implementations, any of the components of the system 100, including the ring 104-*a*, the user device 106-*a* associated with the user 102-*a*, the one or more servers 110, or any combination thereof, may cause the GUI of the user device 106-*a* to display content (e.g., insights about the taggable event and physiological parameter associated with the user 102-*a*) within a time interval after receiving the feedback associated with the identified taggable event or the identified plurality of taggable events. In some cases, the time interval may be preconfigured or selected by the user 102-*a* from a number of time intervals based on preferences of the user 102-*a*. The system 100 may thereby facilitate improvements to the user's 102 general wellness by providing insights according to tags and the user's 102 physiological data.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
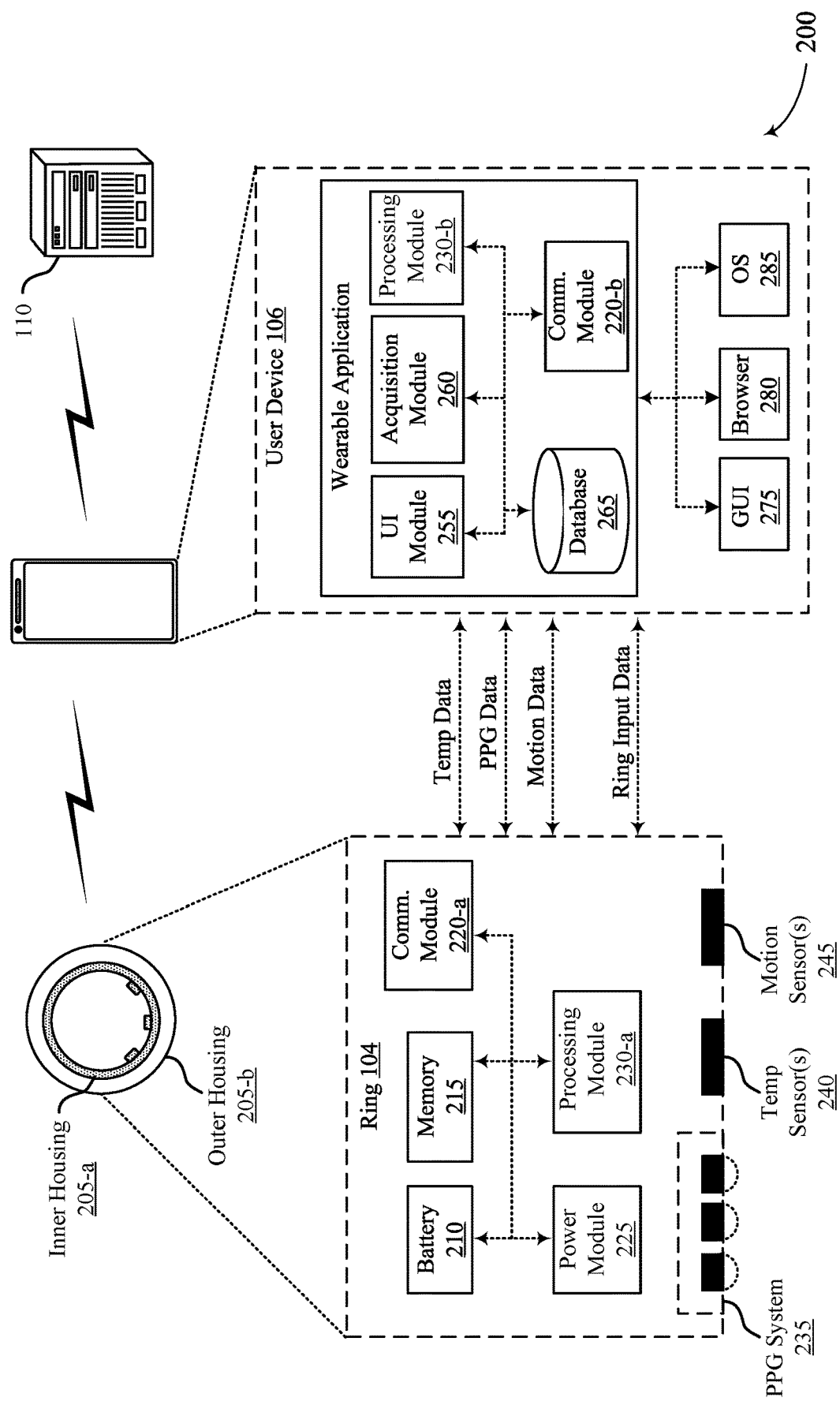

FIG. 2 illustrates an example of a system 200 that supports techniques for providing insights according to tags and physiological data in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

System 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-*a* and an outer housing 205-*b*. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-*a*, a memory 215, a communication module 220-*a*, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-*b* component (e.g., a shell) and an inner housing 205-*a* component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-*b* (e.g., a metal outer housing 205-*b*). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-*b* may be fabricated from one or more materials. In some implementations, the outer housing 205-*b* may include a metal, such as titanium, that may provide strength and abrasion resistance at a relatively light weight. The outer housing 205-*b* may also be fabricated from other materials, such polymers. In some implementations, the outer housing 205-*b* may be protective as well as decorative.

The inner housing 205-*a* may be configured to interface with the user's finger. The inner housing 205-*a* may be formed from a polymer (e.g., a medical grade polymer) or other material. In some implementations, the inner housing 205-*a* may be transparent. For example, the inner housing 205-*a* may be transparent to light emitted by the PPG light emitting diodes (LEDs). In some implementations, the inner housing 205-*a* component may be molded onto the outer housing 205-*a*. For example, the inner housing 205-*a* may include a polymer that is molded (e.g., injection molded) to fit into an outer housing 205-*b* metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage(s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-a. The temperature sensor 240 may be configured to generate a temperature signal (e.g., temperature data) that indicates a temperature read or sensed by the temperature sensor 240. The processing module 230-a may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-a) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-a may use to determine the temperature. As another example, in cases where the temperature sensor 240 includes a passive sensor, the processing module 230-a (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-a may sample the user's temperature over time. For example, the processing module 230-a may sample the user's temperature according to a sampling rate. An example sampling rate may include one sample per second, although the processing module 230-a may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate that may be stored in memory 215 and may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 in which the optical receiver(s) receive transmitted light that is reflected through the region of the user's finger. In some implementations, the PPG system 235 may be configured as a transmissive PPG system 235 in which the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., a Sleep Score, a Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time in which the respective users typically sleep.

In some implementations, each overall score for a user for each respective day (e.g., a Sleep Score, a Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support techniques for physiological pattern recognition. In particular, the system 200 illustrated in FIG. 2 may support techniques for providing insights to a user by causing a user device 106 corresponding to the user to display insights relevant to the user according to tags and physiological data associated with the user. For example, as shown in FIG. 2, a user may be associated with the ring 104 and a user device 106. In this example, the ring 104 may collect physiological data associated with the user, including heart rate, respiratory rate, skin temperature, motion data, and the like. In some aspects, physiological data collected by the ring 104 may be used to determine that at least one physiological parameter (such as a heart rate, a respiratory rate, or the like) associated with the received physiological data satisfies a physiological threshold associated with a pattern between the physiological threshold and a taggable event of a set of taggable events defined within an application associated with the ring 104. The determination may be performed by any of the components of the system 200. For example, the system 200 may have determined over time that there is a pattern for a particular user between a taggable event (e.g., eating after a certain time of day, meditating, etc.) and a physiological parameter exceeding or falling below a physiological threshold (e.g., resting heart rate exceeds 60 bmp, Sleep Score increases by 5 points, etc.).

Upon determining that the at least one physiological parameter associated with the received physiological data satisfies the physiological threshold associated with the pattern between the physiological threshold and the taggable event of the set of taggable events defined within the application associated with the ring 104, the system 200 may identify the taggable event indicating an activity the user engaged in that contributed to the at least one physiological parameter satisfying the physiological threshold. The system 200 may cause the GUI 275 of the user device 106 running the application to prompt the user to provide feedback associated with the identified taggable event or the identified plurality of taggable events. The ability to automatically recognize a taggable event has occurred (or at least the likelihood of a taggable event has exceeded a statistical threshold) based on collected physiological data and to prompt the user to confirm whether the taggable event occurred may increase the user's likelihood to input tags into the system 200 that may enhance the user's experience with the system 200 and enhance the accuracy of the pattern recognition algorithms running in the system 200. The system 200 may receive, via the GUI 275 of the user device 106, a confirmation that the identified taggable event or the identified plurality of taggable events is related to the activity the user engaged in. Alternatively, the system 200 may receive, via the GUI 275 of the user device 106, an indication of a tag associated with the activity in which the user engaged. The tag may be selected by the user from a subset of tags displayed via the GUI 275 with the prompt. The system 200 may thereby facilitate improvements to the user's general wellness by providing insights according to tags and the user's physiological data.

As noted previously herein, the ring 104 of the system 200 may be worn by a user to collect physiological data from the user, including temperature, heart rate, respiration rate, and the like. The ring 104 of the system 200 may collect the physiological data from the user based on arterial blood flow. The physiological data may be collected continuously. In some implementations, the acquisition module 260 may receive the collected physiological data from the ring 104 and forward the physiological data to the processing module 230-b that may determine that the at least one physiological parameter associated with the received physiological data satisfies the physiological threshold associated with the pattern between the physiological threshold and the taggable event or the set of taggable events defined within the application associated with the ring 104. For example, upon receiving the physiological data associated with the user from the ring 104, the processing module 230-b may determine that at least one physiological parameter, such as a heart rate, a respiratory rate, or the like satisfies a physiological parameter threshold during a time interval (e.g., the resting heart rate has exceeded a preconfigured value or has deviated from that user's baseline for more than 10 minutes). Any of the components of the user device 106 may then identify the taggable event indicating an activity the user engaged in that contributed to the at least one physiological parameter satisfying the physiological threshold.

In some aspects, the system 200 may support techniques for receiving a taggable event of a set of taggable events from a user via the ring 104. In other words, the user may indicate a taggable event using the ring 104. One or more taggable events may be associated with one or more gesture controls associated with the ring 104. For example, the user may indicate a taggable event (e.g., that the user just completed meditating) by rotating the ring 104 around the user's finger by a threshold. The amount of rotation of the ring 104 around the user's finger may map to the taggable event. In some other examples, the user may indicate a taggable event (e.g., that the user completed a meal) by tapping on the ring 104 a threshold amount. For example, the user may indicate a taggable event by tapping one or more times on the ring 104. Other examples of gesture controls associated with the ring 104 for indicating a taggable event may be supported by the system 200.

In some cases, any of the components of the system 200 may provide insights according to tags and the user's physiological data. In some implementations, any of the components of the system 200 may generate recommendations for the user (e.g., via the ring 104, the user device 106, or both) based on the tags and the user's physiological data. As such, any of the components of the system 200 may provide insights based on tags. Additionally, any of the components of the system 200 may provide tags based on detected patterns. In some other implementations, any of the components of the system 200 may generate alerts or messages for the user (e.g., via the ring 104, the user device 106, or both) based on the tags and the user's physiological data, where the alerts or messages may provide the insights regarding physiological data of the user as described herein. In some implementations, any of the components of the system 200 may indicate an average number of taggable events identified by users 102. In some implementations, any of the components of the system 200 may determine a number of users 102 (e.g., a percentage of users 102) that engage or dismiss with a prompt to add or confirm one or more taggable events. In some implementations, any of the components of the system 200 may determine and provide the most popular taggable events (e.g., tags) to users 102.

By supporting techniques for providing insights according to tags and physiological data, the system 200 may also generate a more highly structured dataset. This dataset can help the system 200 learn and provide more accurate insights for users 102. Additionally, the system 200 may support better prediction patterns with tags and certain scores contributors, as well as improve learning models (e.g., training recommended tags machine learning model).

Figure 3:
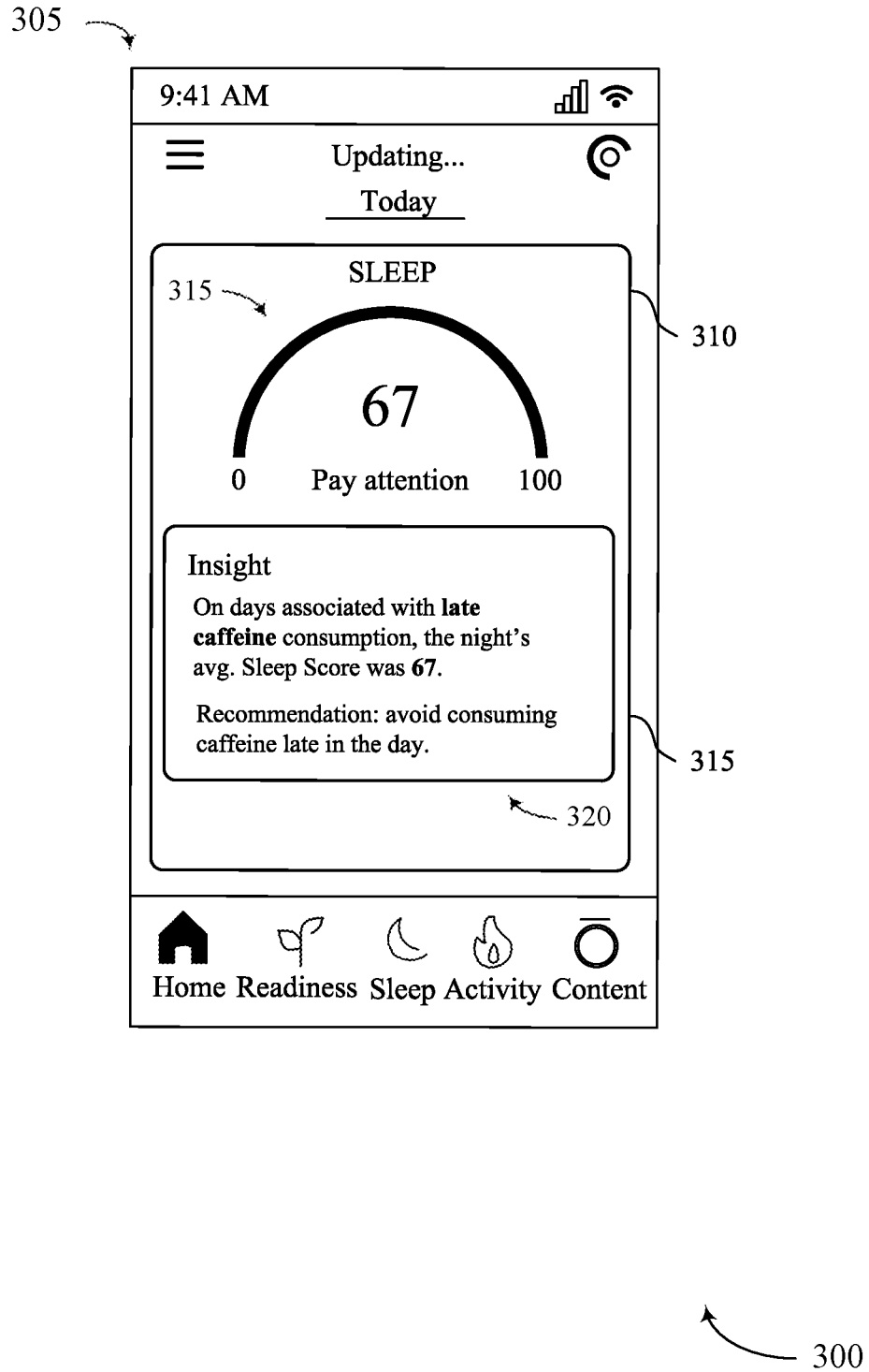
FIGS. 3 and 4 illustrate examples of graphical user interfaces (GUIs) that support techniques for providing insights according to tags and physiological data in accordance with aspects of the present disclosure.

FIG. 3 illustrates an example of a GUI 300 that supports techniques for providing insights according to tags and physiological data in accordance with aspects of the present disclosure. The GUI 300 may implement, or be implemented by, aspects of the system 100 or the system 200, or any combination thereof. In some examples, the GUI 300 may be an example of a GUI of a user device that may be examples of GUIs and user devices as described with reference to FIGS. 1 and 2. For example, the GUI 300 may be an example of a GUI 275 of a user device 106 as described with reference to FIGS. 1 and 2. In the example of FIG. 3, the GUI 300 may include an application interface 305 that may be displayed to a user 102 via the GUI 300.

The application interface 305 may be associated with an application running on a user device 106. In some examples, the application interface 305 may include a set of graphical elements (also referred to as widgets or components) the application provides so that a user 102 may provide input to, and receive output from, the application via the application interface 305. In some examples, one or more operations associated with the GUI 300 may be performed based on a manipulation of the one or more graphical elements associated with the GUI 300. Examples of graphical elements associated with the GUI 300 may include, but are not limited to, buttons, sliders, droplists, tabs, text boxes, and the like. The application interface 305 may also include a set of tabs enabling the user 102 to switch between different features of the application. For example, the set of tabs may allow the user 102 to switch between one or more of a "home feature," a "readiness feature," a "sleep feature," an "activity feature", or a "content feature" in the application running on the user device 106.

As noted previously, physiological data collected from the user 102 along with taggable events tagged by the user 102 may be used to calculate a score and/or a metric (e.g., a Sleep Score, a Readiness Score) for the user 102. The calculated score and/or metric may be displayed to the user 102 via the GUI 300, as shown in the application interface 305. For example, the application interface 305 may include a graphical element 310 that may display one or more of a Sleep Score 315 or a message 320. In some examples, the message 320 may be an insight that is relevant to physiological data and taggable events, and their contribution to the Sleep Score 315 associated with the user 102. In the example of FIG. 3, the insight may be that "On days associated with late caffeine consumption, the night's average Sleep Score was 67." Additionally, the message 320 may provide a recommendation to the user 102 based on the insight relevant to physiological data and taggable events. In the example of FIG. 3, the recommendation may be to "avoid consuming caffeine late in the day."

In some implementations, the GUI 300 may also display patterns associated with the insight relevant to physiological data and taggable events. In some examples, the pattern may indicate a relationship between an activity in which the user 102 engaged (e.g., workouts) and a Readiness Score for the user 102. In some other examples, the pattern may indicate a relationship between another activity in which the user 102 engaged (e.g., bedtime consistency) and the Sleep Score 315 for the user 102. The pattern may be displayed via another graphical element of the GUI 300, such as a pattern context card that may include providing the additional insights relevant to physiological data and taggable events.

Therefore, the GUI 300 may provide personalized insight relevant to physiological data and taggable events, and their contribution to a respective Health Score (e.g., the Sleep Score 315) associated with the user 102. As such, the GUI 300 may be configured to support tags in insights that may consist of text-based insight messages that reference a tag from a previous time interval (e.g., day, week, month, etc.), the impact it had, and guidance associated with the tag. Put another way, a user 102 may be able to provide additional context information on what has contributed to changes in the user's general wellness (e.g., a user's Readiness Score, a user's Sleep Score). In return, the user 102 may be able to better understand the relationship between certain taggable events (e.g., tags) and how these might affect the user's 102 general wellness (e.g., the user's Readiness Score, the user's Sleep Score). By providing personalized insights to the user 102 triggered by physiological data associated with the user 102, the user 102 may experience an improvement to one or more physiological parameters (e.g., heart rate, respiratory rate, and the like) that may improve the user's general wellness.

Figure 4:
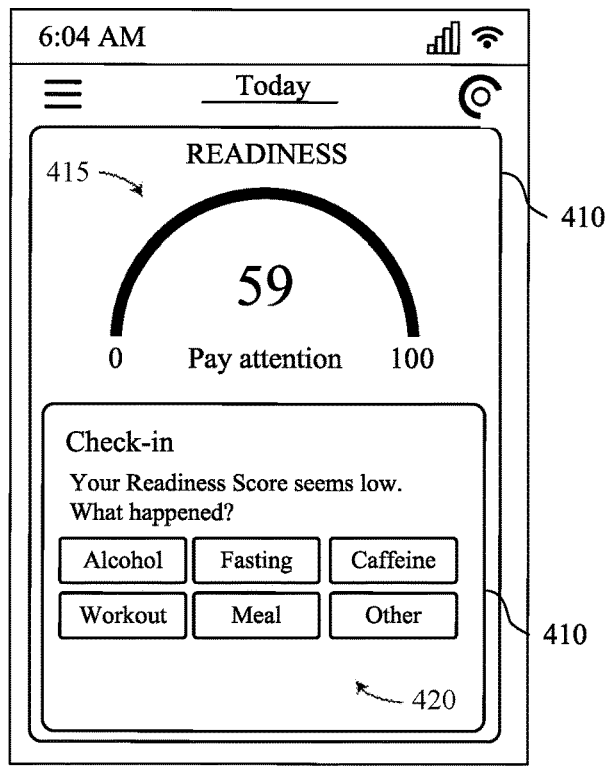
Figure 4:
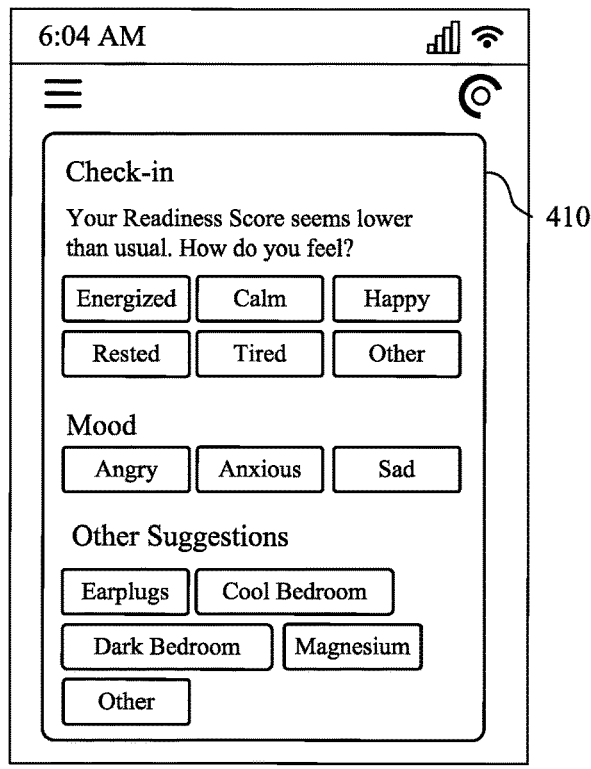

FIG. 4 illustrates an example of a GUI 400 that supports techniques for providing insights according to tags and physiological data in accordance with aspects of the present disclosure. The GUI 400 may implement, or be implemented by, aspects of the system 100 or the system 200, or any combination thereof. In some examples, the GUI 400 may be an example of a GUI of a user device that may be examples of GUIs and user devices as described with reference to FIGS. 1 and 2. For example, the GUI 400 may be an example of a GUI 275 of a user device 106 as described with reference to FIGS. 1 and 2. In the example of FIG. 4, the GUI 400 may include a sequence of applications interfaces including one or more of an application interface 405-a and an application interface 405-b that may be displayed to a user 102 via the GUI 400.

The application interface 405-a may be associated with an application (e.g., a wellness application) running on a user device 106. In some examples, the application interface 405-a may include a set of graphical elements the application provides so that a user 102 may provide input to, and receive output from, the application via the application interface 405-a. For example, the application interface 405-a may include one or both of a graphical element 410 that may display a Readiness Score 415 or a graphical element 410 that may display a check-in message 420. The check-in message 420 may include a message, such as "Your Deep Sleep was low last night. What happened?" and prompt the user 102 to provide feedback by selecting a tag associated with an activity the user 102 engaged in that may have contributed to the Readiness Score 415. The tag may be selected from a subset of tags displayed via the graphical element 410.

Put another way, the GUI 400 may indicate whether a user's 102 Readiness Score or Sleep Score had a positive or negative change, and prompt the user 102 to reflect what may have contributed to it (e.g., the activity the user engaged in). In some implementations, the GUI 400 may trigger (e.g., prompt) a user 102 to the user 102 to provide feedback by selecting a tag associated with an activity the user 102 engaged in that may have contributed to the user's 102 Readiness Score 415 (or Sleep Score) when the user 102 has a higher Readiness Score 415 (or Sleep Score) compared to a baseline Readiness Score (or baseline Sleep Score). In some other implementations, the GUI 400 may trigger (e.g., prompt) a user 102 to the user 102 to provide feedback by selecting a tag associated with an activity the user 102 engaged in that may have contributed to the user's 102 Readiness Score 415 (or Sleep Score) when the user 102 has a lower Readiness Score 415 (or Sleep Score) compared to a baseline Readiness Score (or baseline Sleep Score). In other implementations, the GUI 400 may trigger (e.g., prompt) a user 102 to the user 102 to provide feedback by selecting a tag associated with an activity the user 102 engaged in that may have contributed to the user's 102 Readiness Score 415 (or Sleep Score) when the user 102 has both a higher or lower Readiness Score 415 (or Sleep Score) compared to a baseline Readiness Score (or baseline Sleep Score).

In the example of FIG. 4, a tag may include, but is not limited to, "Alcohol," "Fasting," "Caffeine," "Workout," "Meal," or "Other." In some examples, the subset of tags may be determined or retrieved based on historical data of lifestyle choices associated with the user 102 (e.g., that contribute to lesser deep sleep). In some other examples, the subset of tags may be determined or retrieved based on observed patterns from that user's 102 life (e.g., based on previous inputs). In other examples, the subset of tags may be determined or retrieved based on crowdsourcing patterns among all users of similar demographics.

In some implementations, the application interface 405-b may provide the user 102 with additional tags displayed via the graphical element 410. Put another way, the GUI 400 may provide additional tags to the user 102 and the user 102 may review and engage with the additional tags. In some implementations, the additional tags displayed via the graphical element 410 may relate to an energy level the user 102 is feeling. For example, the additional tags may include, but are not limited to, "Energized," "Calm," "Happy," "Rested," "Tired," or "Other." In some other implementations, the additional tags displayed via the graphical element 410 may relate to a mood the user 102 is feeling. For example, the additional tags may include, but are not limited to, "Angry," "Anxious," and "Sad," among other examples. In other implementations, the additional tags displayed via the graphical element 410 may relate to other taggable contributors for the Readiness Score 415. For example, the additional tags may include, but are not limited to, "Earplugs," "Cool Bedroom," "Dark Bedroom," "Magnesium," or "Other," among other examples. The application interface 405-*a* may display to a user 102 recent tags, including one or more tags the user 102 previously added within a time interval (e.g., within the past 2 months).

In some implementations, the application interface 405-*a* may display to a user 102 tags that had a threshold change (e.g., a >5% median difference) to a baseline Score for one or more users 102. In some implementations, the application interface 405-*a* may display to a user 102 tags that had an impact for a threshold number of users 102 (e.g., at least 500 users). In some implementations, the application interface 405-*a* may display to a user 102 tags that were considered positive or negative.

In some implementations, if a user 102 adds a tag, the user 102 may be "reward" with an insight card that acknowledges a tag was added, as well as additional insights about the tag. For example, the application interface 405-*a* may indicate a correlation between the user's 102 scores and when they add tags. In some implementations, tags may be added to a Weekly Report to highlight and help the user 102 reflect on the user's 102 weekly tag behavior. In some implementations, if the user 102 adds a tag, the application interface 405-*a* may show a reward message that includes a health insight for the user 102. In some implementations, if the user 102 previously added the same tag, the application interface 405-*a* may show a default reward message that includes a health insight for the user 102. In some implementations, the application interface 405-*a* may assign the date and time for a user 102 provided tag. For example, the application interface 405-*a* may assign a date/time as default to the time the user 102 when the user 102 added the tag.

In some implementations, the application interface 405-*a* may prompt a user 102 periodically or aperiodically to provide feedback by selecting a tag associated with an activity the user 102 engaged in that may have contributed to the Readiness Score 415 or a Sleep Score as described with reference in FIG. 3. In some implementations, the application interface 405-*a* may prompt a user 102 periodically or aperiodically to provide feedback by selecting a tag associated with an activity the user 102 engaged in when there is a significant change (e.g., a threshold percent change) to the user's 102 the Readiness Score 415 or a Sleep Score. In some implementations, the application interface 405-*a* may prompt a user 102 to provide feedback by selecting a tag associated with an activity the user 102 engaged in when the user 102 has achieved a positive change to their baseline Readiness Score or baseline Sleep Score. This may create a delightful, celebratory moment for the user 102 and as a result, leading to an increase in tags added to the system. In some other implementations, the application interface 405-*a* may prompt a user 102 to provide feedback by selecting a tag associated with an activity the user 102 engaged in when the user 102 has both positive and negative changes to their baseline Readiness Score or baseline Sleep Score. This may result in more relevant insight to user 102 through additional moments of reflection and a wider range of personalized tags; leading to an increase in tags added.

As described herein, any of the components of the system 100 and/or the system 200, including a ring 104, a user device 106 associated with a user 102, the one or more servers 110, or any combination thereof, may provide an insight that is relevant to physiological data and the tags selected by the user 102, and their contribution to the Readiness Score 415 associated with the user 102. In some implementations, as described herein, any of the components of the system 100 and/or the system 200, including a ring 104, a user device 106 associated with a user 102, the one or more servers 110, or any combination thereof, may determine a pattern between a physiological threshold and a taggable event. Any of the components of the system 100 and/or the system 200, including a ring 104, a user device 106 associated with a user 102, the one or more servers 110, or any combination thereof, may determine a pattern by performing an analysis that identifies common patterns between lifestyle choices of the user 102 (e.g., activities the user 102 engages in) and health-related metrics (e.g., sleep metrics, and the like) associated with the user 102. With the use of tags, any of the components of the system 100 and/or the system 200 may estimate the influence that the lifestyle choices behind the tags might have had on well-being for the user 102.

In some implementations, any of the components of the system 100 and/or the system 200, including a ring 104, a user device 106 associated with a user 102, the one or more servers 110, or any combination thereof, may determine a set of first timestamps associated with the at least one physiological parameter (such as a heart rate, a respiratory rate, or the like) satisfying the physiological threshold and a set of second timestamps associated with a received tag (e.g., "Alcohol," "Fasting," "Caffeine," "Workout," "Meal," or "Other") via the graphical element 410. The received tag may be selected by the user 102 from the set of tags (e.g., "Alcohol," "Fasting," "Caffeine," "Workout," "Meal," or "Other"). Based on the determination, any of the components of the system 100 and/or the system 200, including a ring 104, a user device 106 associated with a user 102, the one or more servers 110, or any combination thereof, may determine the pattern between the physiological threshold and the taggable event or the plurality of taggable events based at least in part on a temporal relationship between the set of first timestamps and the set of second timestamps. In some implementations, any of the components of the system 100 and/or the system 200, including a ring 104, a user device 106 associated with a user 102, the one or more servers 110, or any combination thereof, may determine a temporal difference between the set of first timestamps and the set of second timestamps, and determine that the temporal difference between the set of first timestamps and the set of second timestamps satisfies a correlation threshold. As a result, any of the components of the system 100 and/or the system 200, including a ring 104, a user device 106 associated with a user 102, the one or more servers 110, or any combination thereof, may determine the pattern between the physiological threshold and the taggable event or the plurality of taggable events (e.g., "Alcohol," "Fasting," "Caffeine," "Workout," "Meal," or "Other") based at least in part on determining that the temporal difference between the set of first timestamps and the set of second timestamps satisfies the correlation threshold.

Any of the components of the system 100 and/or the system 200, including a ring 104, a user device 106 associated with a user 102, the one or more servers 110, or any combination thereof, may determine the pattern between the physiological threshold and the taggable event or the plurality of taggable events (e.g., "Alcohol," "Fasting," "Caffeine," "Workout," "Meal," or "Other") by inputting one or more respective physiological parameters associated with respective physiological data collected previously and one or more respective tags of the set of tags selected by the user 102 into a machine learning model. The machine learning model may be trained to identify temporal relationships between the respective physiological parameters and each respective tag of the one or more respective tags of the set of tags selected by the user 102. In some implementations, any of the components of the system 100 and/or the system 200, including a ring 104, a user device 106 associated with a user 102, the one or more servers 110, or any combination thereof, may filter tags to avoid presenting the tags to a user 102 based on whether the user's 102 experienced both positive and/or negative changes to their baseline Readiness Score or baseline Sleep Score.

Therefore, the GUI 400 may provide personalized insights relevant to physiological data and taggable events, and their contribution to a respective Health Score (e.g., the Readiness Score 415) associated with the user 102. By providing personalized insights to the user 102 triggered by physiological data associated with the user 102, the user 102 may experience an improvement to one or more physiological parameters (e.g., heart rate, respiratory rate, and the like) that may improve the user's general wellness.

Figure 5:
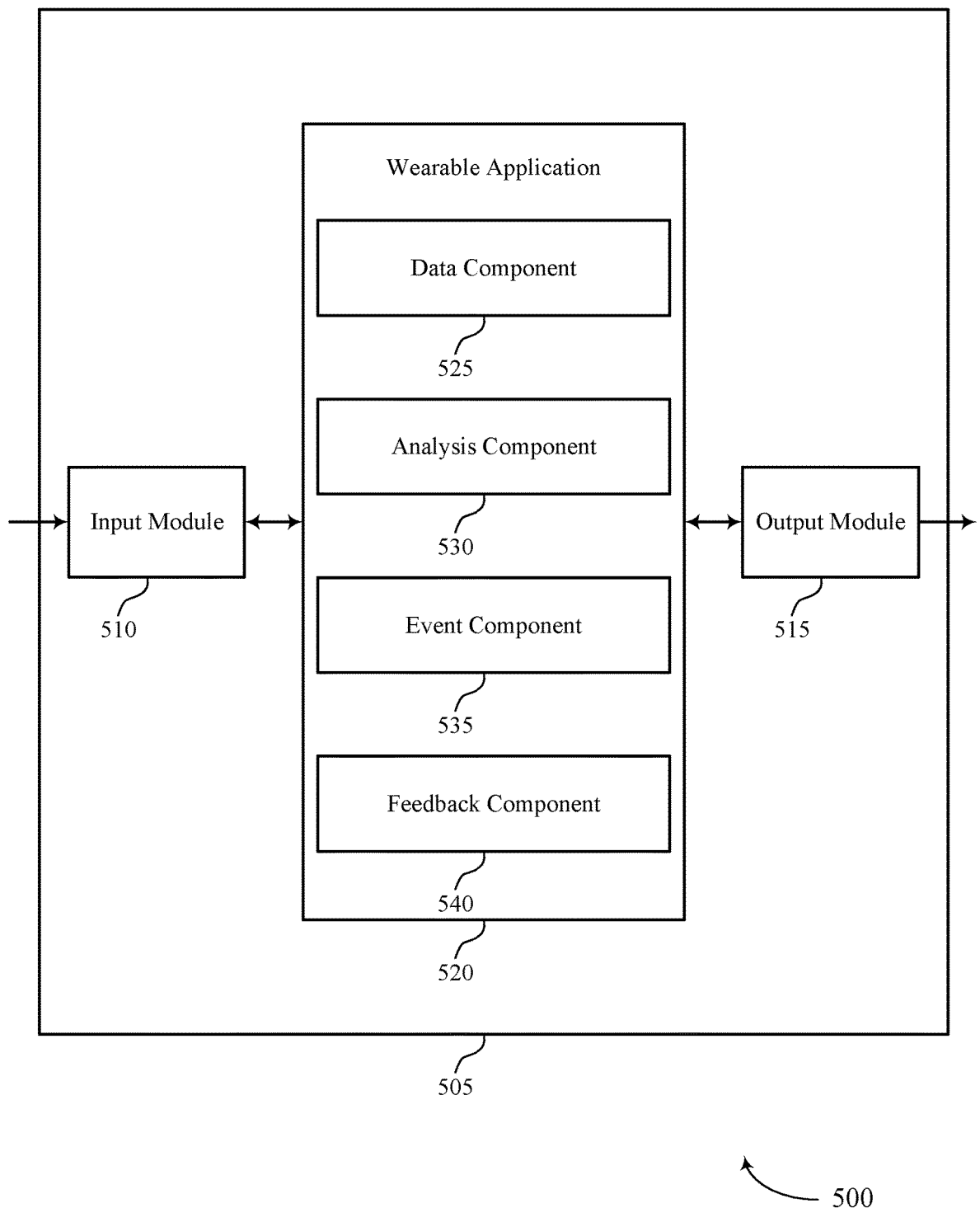
FIG. 5 shows a block diagram of an apparatus that supports techniques for providing insights according to tags and physiological data in accordance with aspects of the present disclosure.

FIG. 5 shows a block diagram 500 of a device 505 that supports techniques for providing insights according to tags and physiological data in accordance with aspects of the present disclosure. The device 505 may include an input module 510, an output module 515, and a wearable application 520. The device 505 may also include a processor. Each of these components may be in communication with one another (e.g., via one or more buses).

The input module 510 may provide a means for receiving information such as packets, user data, control information, or any combination thereof associated with various information channels (e.g., control channels, data channels, information channels related to illness detection techniques). Information may be passed on to other components of the device 505. The input module 510 may utilize a single antenna or a set of multiple antennas.

The output module 515 may provide a means for transmitting signals generated by other components of the device 505. For example, the output module 515 may transmit information such as packets, user data, control information, or any combination thereof associated with various information channels (e.g., control channels, data channels, information channels related to illness detection techniques). In some examples, the output module 515 may be co-located with the input module 510 in a transceiver module. The output module 515 may utilize a single antenna or a set of multiple antennas.

For example, the wearable application 520 may include a data component 525, an analysis component 530, an event component 535, a feedback component 540, or any combination thereof. In some examples, the wearable application 520, or various components thereof, may be configured to perform various operations (e.g., receiving, monitoring, transmitting) using or otherwise in cooperation with the input module 510, the output module 515, or both. For example, the wearable application 520 may receive information from the input module 510, send information to the output module 515, or be integrated in combination with the input module 510, the output module 515, or both to receive information, transmit information, or perform various other operations as described herein.

The wearable application 520 may support physiological pattern recognition in accordance with examples as disclosed herein. The data component 525 may be configured as or otherwise support a means for receiving physiological data associated with a user from a wearable device. The analysis component 530 may be configured as or otherwise support a means for determining that at least one physiological parameter associated with the received physiological data satisfies a physiological threshold associated with a pattern between the physiological threshold and a taggable event or a plurality of taggable events defined within an application associated with the wearable device. The event component 535 may be configured as or otherwise support a means for identifying, based at least in part on the pattern, the taggable event or the plurality of taggable events indicating an activity in that the user engaged that contributed to the at least one physiological parameter satisfying the physiological threshold. The feedback component 540 may be configured as or otherwise support a means for causing a GUI of the device 505 running the application to prompt the user to provide feedback associated with the identified taggable event or the identified plurality of taggable events.

Figure 6:
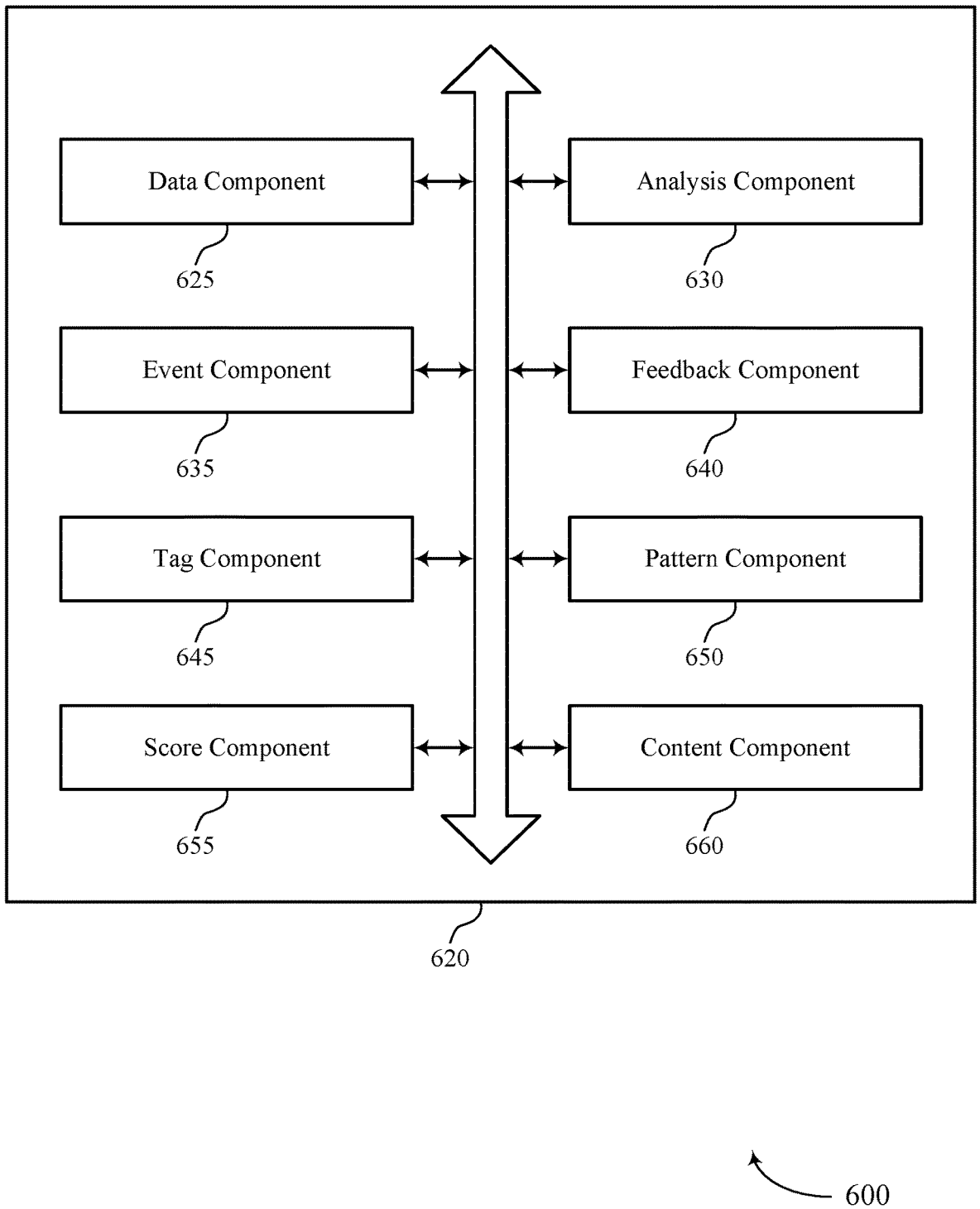
FIG. 6 shows a block diagram of a wearable application that supports techniques for providing insights according to tags and physiological data in accordance with aspects of the present disclosure.

FIG. 6 shows a block diagram 600 of a wearable application 620 that supports techniques for providing insights according to tags and physiological data in accordance with aspects of the present disclosure. The wearable application 620 may be an example of aspects of a wearable application or a wearable application 520, or both, as described herein. The wearable application 620, or various components thereof, may be an example of means for performing various aspects of techniques for providing insights according to tags and physiological data as described herein. For example, the wearable application 620 may include a data component 625, an analysis component 630, an event component 635, a feedback component 640, a tag component 645, a pattern component 650, a score component 655, a content component 660, or any combination thereof. Each of these components may communicate, directly or indirectly, with one another (e.g., via one or more buses).

The wearable application 620 may support physiological pattern recognition in accordance with examples as disclosed herein. The data component 625 may be configured as or otherwise support a means for receiving physiological data associated with a user from a wearable device. The analysis component 630 may be configured as or otherwise support a means for determining that at least one physiological parameter associated with the received physiological data satisfies a physiological threshold associated with a pattern between the physiological threshold and a taggable event or a plurality of taggable events defined within an application associated with the wearable device. The event component 635 may be configured as or otherwise support a means for identifying, based at least in part on the pattern, the taggable event or the plurality of taggable events indicating an activity the user engaged in that contributed to the at least one physiological parameter satisfying the physiological threshold. The feedback component 640 may be configured as or otherwise support a means for causing a GUI of a device running the application to prompt the user to provide feedback associated with the identified taggable event or the identified plurality of taggable events.

In some examples, the feedback component 640 may be configured as or otherwise support a means for receiving, via the GUI and based at least in part on prompting the user to provide the feedback, a confirmation that the identified taggable event or the identified plurality of taggable events is related to the activity in which the user engaged. In some examples, the tag component 645 may be configured as or otherwise support a means for receiving, via the GUI, an indication of a tag associated with the activity in which the user engaged. In some examples, the tag is selected from a subset of tags displayed via the GUI with the prompt. In some examples, the feedback includes the received tag selected from the subset of tags.

In some examples, the pattern component 650 may be configured as or otherwise support a means for determining the pattern between the physiological threshold and the taggable event or the plurality of taggable events. In some examples, the pattern component 650 may be configured as or otherwise support a means for determining a plurality of first timestamps associated with the at least one physiological parameter satisfying the physiological threshold and a plurality of second timestamps associated with a received tag, wherein the received tag is selected by the user from the plurality of tags. In some examples, the pattern component 650 may be configured as or otherwise support a means for determining the pattern between the physiological threshold and the taggable event or the plurality of taggable events based at least in part on a temporal relationship between the plurality of first timestamps and the plurality of second timestamps.

In some examples, the pattern component 650 may be configured as or otherwise support a means for determining a temporal difference between the plurality of first timestamps and the plurality of second timestamps. In some examples, the pattern component 650 may be configured as or otherwise support a means for determining that the temporal difference between the plurality of first timestamps and the plurality of second timestamps satisfies a correlation threshold. In some examples, the pattern component 650 may be configured as or otherwise support a means for determining the pattern between the physiological threshold and the taggable event or the plurality of taggable events is based at least in part on determining that the temporal difference between the plurality of first timestamps and the plurality of second timestamps satisfies the correlation threshold.

In some examples, to support determining the pattern between the physiological threshold and the taggable event or the plurality of taggable events, the pattern component 650 may be configured as or otherwise support a means for inputting one or more respective physiological parameters associated with respective physiological data collected previously from the wearable device and one or more respective tags of the plurality of tags selected previously by the user into a machine learning model. In some examples, the machine learning model is trained to identify temporal relationships between the respective physiological parameters and each respective tag of the one or more respective tags of the plurality of tags selected previously by the user. In some examples, the pattern component 650 may be configured as or otherwise support a means for updating the pattern between the physiological threshold and the taggable event or the plurality of taggable events based at least in part on inputting subsequently received physiological data from the wearable device or the subsequently received tags associated with the activity in which the user engaged into the machine learning model.

In some examples, the pattern component 650 may be configured as or otherwise support a means for inputting one or more respective physiological parameters associated with respective physiological data collected previously from a plurality of users and one or more respective tags of the plurality of tags selected previously by the plurality of users into a machine learning model. In some examples, the pattern component 650 may be configured as or otherwise support a means for determining the pattern between the physiological threshold and the taggable event or the plurality of taggable events based at least in part on inputting the one or more respective physiological parameters and the one or more respective tags of the plurality of tags selected previously by the plurality of users into the machine learning model. In some examples, the pattern component 650 may be configured as or otherwise support a means for determining a baseline value of the at least one physiological parameter associated with the received physiological data. In some examples, the pattern component 650 may be configured as or otherwise support a means for determining the pattern between the physiological threshold and the taggable event or the plurality of taggable events based at least in part on determining the baseline value of the at least one physiological parameter associated with the received physiological data.

In some examples, the pattern component 650 may be configured as or otherwise support a means for causing the GUI of the device running the application to provide to the user an insight identifying a relationship between the activity in which the user engaged and a metric associated with the user (e.g., a Readiness Score or a Sleep Score, or both), based at least in part on the identified taggable event or the identified plurality of taggable events. In some examples, the relationship further comprises activity information indicating a type of the activity the user engaged in, timing information indicating a timestamp of the activity the user engaged in, location information indicating a locality of the activity the user engaged in, or any combination thereof that contributed to the metric associated with the user. In some examples the insight further includes a recommendation for adjusting the metric associated with the user.

In some examples, the score component 655 may be configured as or otherwise support a means for tracking a set of Scores by monitoring one or more activities the user engaged in and one or more identified tags provided to or selected by the user that contribute to the set of Scores throughout a time interval. In some examples, the score component 655 may be configured as or otherwise support a means for updating the set of Scores based at least in part on tracking the set of Scores throughout the time interval. In some examples, the content component 660 may be configured as or otherwise support a means for causing the GUI of the device to output content based at least in part on updating the set of Scores. In some examples, the content component 660 may be configured as or otherwise support a means for causing the GUI of the device to display content within a time interval after receiving the feedback associated with the identified taggable event or the identified plurality of taggable events, wherein the time interval is preconfigured or selected from a plurality of time intervals.

In some examples, the at least one physiological parameter associated with the received physiological data includes heart rate data associated with the user, heart rate variability data associated with the user, temperature data associated with the user, respiratory rate data associated with the user, blood oxygen data associated with the user, sleep data associated with the user, activity data associated with the user, or any combination thereof. In some examples, the wearable device includes a wearable ring device.

Figure 7:
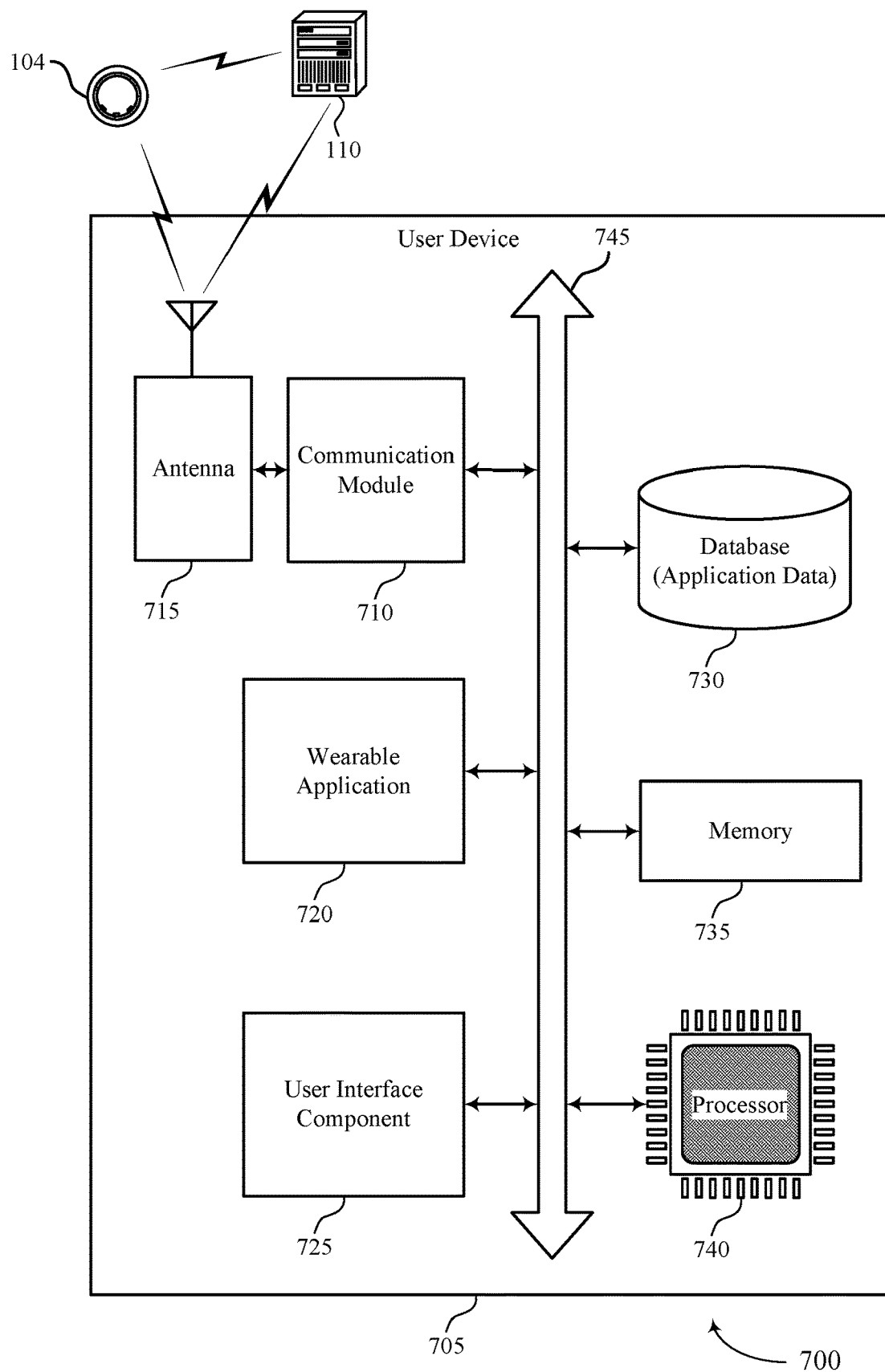
FIG. 7 shows a diagram of a system including a device that supports techniques for providing insights according to tags and physiological data in accordance with aspects of the present disclosure.

FIG. 7 shows a diagram of a system 700 including a device 705 that supports techniques for providing insights according to tags and physiological data in accordance with aspects of the present disclosure. The device 705 may be an example of or include the components of a device 505 as described herein. The device 705 may include an example of a user device 106, as described previously herein. The device 705 may include components for bi-directional communications including components for transmitting and receiving communications with a wearable device 104 and a server 110, such as a wearable application 720, a communication module 710, an antenna 715, a user interface component 725, a database (application data) 730, a memory 735, and a processor 740. These components may be in electronic communication or otherwise coupled (e.g., operatively, communicatively, functionally, electronically, electrically) via one or more buses (e.g., a bus 745).

The communication module 710 may manage input and output signals for the device 705 via the antenna 715. The communication module 710 may include an example of the communication module 220-b of the user device 106 shown and described in FIG. 2. In this regard, the communication module 710 may manage communications with the ring 104 and the server 110, as illustrated in FIG. 2. The communication module 710 may also manage peripherals not integrated into the device 705. In some cases, the communication module 710 may represent a physical connection or port to an external peripheral. In some cases, the communication module 710 may utilize an operating system such as iOS®, ANDROID®, MS-DOS®, MS-WINDOWS®, OS/2®, UNIX®, LINUX®, or another known operating system. In other cases, the communication module 710 may represent or interact with a wearable device (e.g., ring 104), modem, a keyboard, a mouse, a touchscreen, or a similar device. In some cases, the communication module 710 may be implemented as part of the processor 740. In some examples, a user may interact with the device 705 via the communication module 710, user interface component 725, or via hardware components controlled by the communication module 710.

In some cases, the device 705 may include a single antenna 715. However, in some other cases, the device 705 may have more than one antenna 715 that may be capable of concurrently transmitting or receiving multiple wireless transmissions. The communication module 710 may communicate bi-directionally, via the one or more antennas 715, wired, or wireless links as described herein. For example, the communication module 710 may represent a wireless transceiver and may communicate bi-directionally with another wireless transceiver. The communication module 710 may also include a modem to modulate the packets, to provide the modulated packets to one or more antennas 715 for transmission, and to demodulate packets received from the one or more antennas 715.

The user interface component 725 may manage data storage and processing in a database 730. In some cases, a user may interact with the user interface component 725. In other cases, the user interface component 725 may operate automatically without user interaction. The database 730 may be an example of a single database, a distributed database, multiple distributed databases, a data store, a data lake, or an emergency backup database.

The memory 735 may include RAM and ROM. The memory 735 may store computer-readable, computer-executable software including instructions that, when executed, cause the processor 740 to perform various functions described herein. In some cases, the memory 735 may contain, among other things, a BIOS that may control basic hardware or software operation such as the interaction with peripheral components or devices.

The processor 740 may include an intelligent hardware device, (e.g., a general-purpose processor, a DSP, a CPU, a microcontroller, an ASIC, an FPGA, a programmable logic device, a discrete gate or transistor logic component, a discrete hardware component, or any combination thereof). In some cases, the processor 740 may be configured to operate a memory array using a memory controller. In other cases, a memory controller may be integrated into the processor 740. The processor 740 may be configured to execute computer-readable instructions stored in a memory 735 to perform various functions (e.g., functions or tasks supporting a method and system for sleep staging algorithms).

The wearable application 720 may support physiological pattern recognition in accordance with examples as disclosed herein. For example, the wearable application 720 may be configured as or otherwise support a means for receiving physiological data associated with a user from a wearable device. The wearable application 720 may be configured as or otherwise support a means for determining that at least one physiological parameter associated with the received physiological data satisfies a physiological threshold associated with a pattern between the physiological threshold and a taggable event or a plurality of taggable events defined within an application associated with the wearable device.

The wearable application 720 may be configured as or otherwise support a means for identifying, based at least in part on the pattern, the taggable event or the plurality of taggable events indicating an activity the user engaged in that contributed to the at least one physiological parameter satisfying the physiological threshold. The wearable application 720 may be configured as or otherwise support a means for causing a GUI of the device 705 running the application to prompt the user to provide feedback associated with the identified taggable event or the identified plurality of taggable events. By including or configuring the wearable application 720 in accordance with examples as described herein, the device 705 may support techniques for reduced latency, improved user experience related to reduced processing, reduced power consumption, and improved utilization of processing capability.

The wearable application 720 may include an application (e.g., "app"), program, software, or other component that is configured to facilitate communications with a ring 104, server 110, other user devices 106, and the like. For example, the wearable application 720 may include an application executable on a user device 106 that is configured to receive data (e.g., physiological data) from a ring 104, perform processing operations on the received data, transmit and receive data with the servers 110, and cause presentation of data to a user 102.

Figure 8:
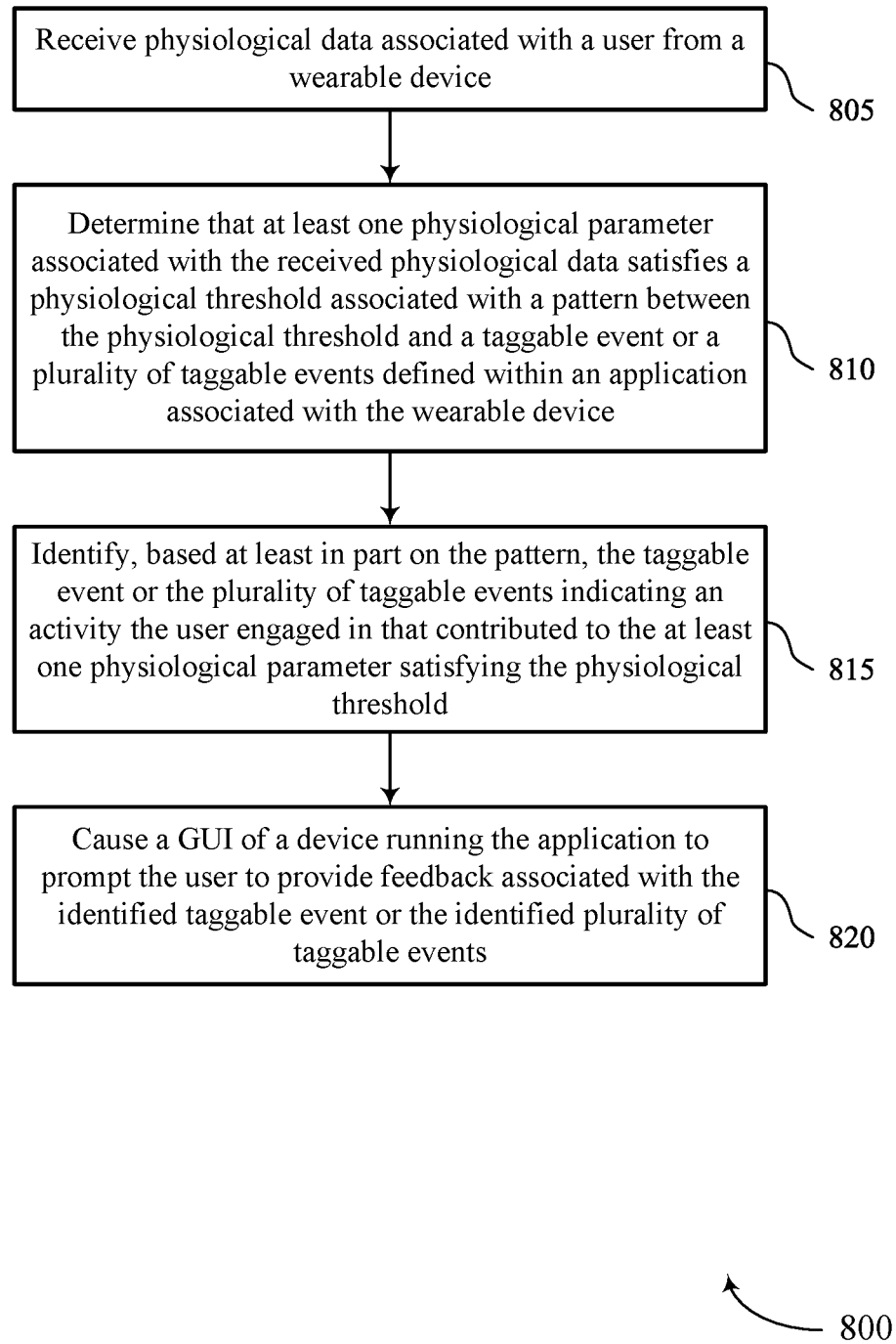
FIGS. 8 through 12 show flowcharts illustrating methods that support techniques for providing insights according to tags and physiological data in accordance with aspects of the present disclosure.

FIG. 8 shows a flowchart illustrating a method 800 that supports techniques for providing insights according to tags and physiological data in accordance with aspects of the present disclosure. The operations of the method 800 may be implemented by a user device or its components as described herein. For example, the operations of the method 800 may be performed by a user device as described with reference to FIGS. 1 through 7. In some examples, a user device may execute a set of instructions to control the functional elements of the user device to perform the described functions. Additionally or alternatively, a user device may perform aspects of the described functions using special-purpose hardware.

At 805, the method may include receiving physiological data associated with a user from a wearable device. The operations of 805 may be performed in accordance with examples as disclosed herein. In some examples, aspects of the operations of 805 may be performed by a data component 625 as described with reference to FIG. 6.

At 810, the method may include determining that at least one physiological parameter associated with the received physiological data satisfies a physiological threshold associated with a pattern between the physiological threshold and a taggable event or a plurality of taggable events defined within an application associated with the wearable device. The operations of 810 may be performed in accordance with examples as disclosed herein. In some examples, aspects of the operations of 810 may be performed by an analysis component 630 as described with reference to FIG. 6.

At 815, the method may include identifying, based at least in part on the pattern, the taggable event or the plurality of taggable events indicating an activity the user engaged in that contributed to the at least one physiological parameter satisfying the physiological threshold. The operations of 815 may be performed in accordance with examples as disclosed herein. In some examples, aspects of the operations of 815 may be performed by an event component 635 as described with reference to FIG. 6.

At 820, the method may include causing a GUI of a device running the application to prompt the user to provide feedback associated with the identified taggable event or the identified plurality of taggable events. The operations of 820 may be performed in accordance with examples as disclosed herein. In some examples, aspects of the operations of 820 may be performed by a feedback component 640 as described with reference to FIG. 6.

Figure 9:
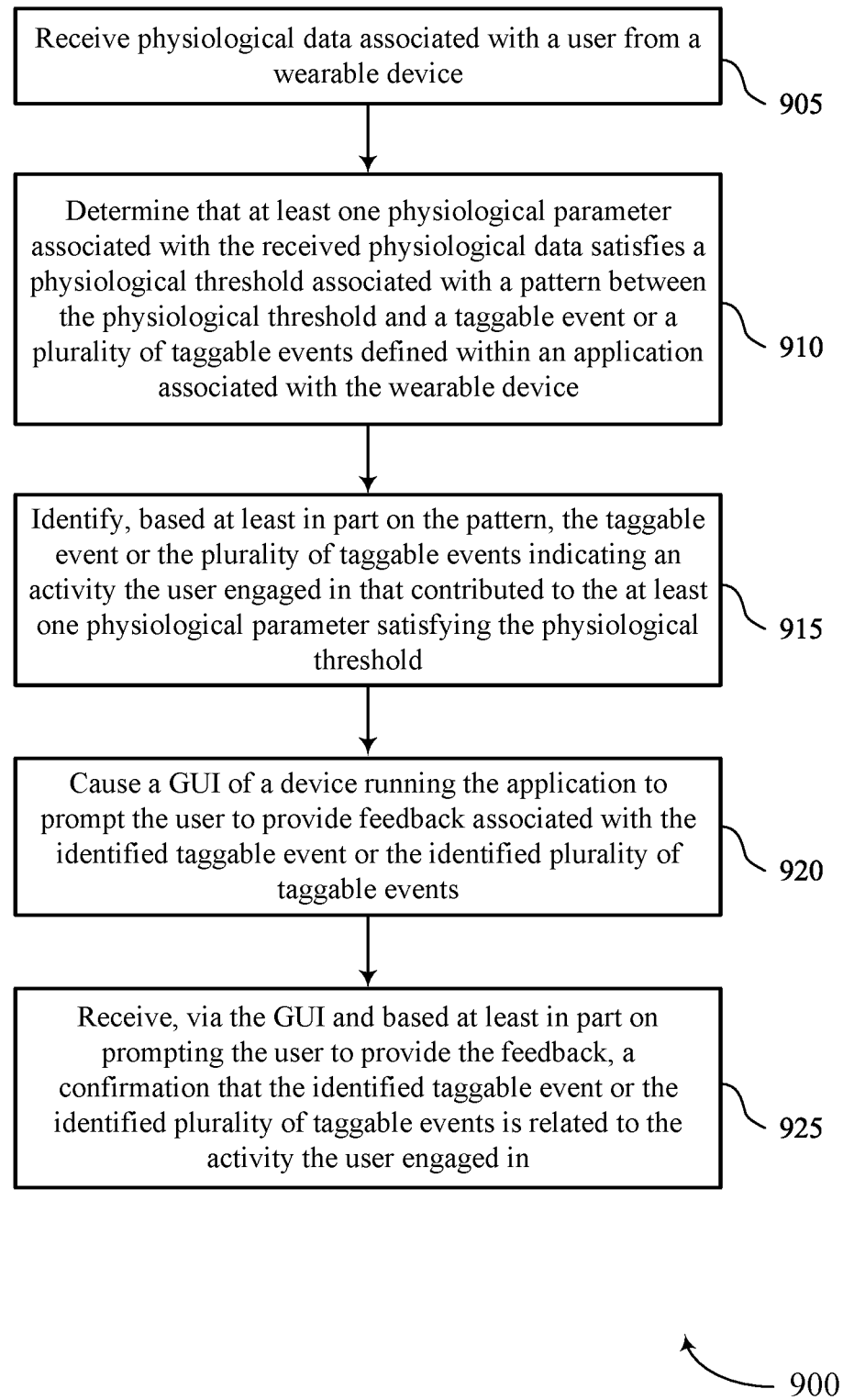

FIG. 9 shows a flowchart illustrating a method 900 that supports techniques for providing insights according to tags and physiological data in accordance with aspects of the present disclosure. The operations of the method 900 may be implemented by a user device or its components as described herein. For example, the operations of the method 900 may be performed by a user device as described with reference to FIGS. 1 through 7. In some examples, a user device may execute a set of instructions to control the functional elements of the user device to perform the described functions. Additionally or alternatively, the user device may perform aspects of the described functions using special-purpose hardware.

At 905, the method may include receiving physiological data associated with a user from a wearable device. The operations of 905 may be performed in accordance with examples as disclosed herein. In some examples, aspects of the operations of 905 may be performed by a data component 625 as described with reference to FIG. 6.

At 910, the method may include determining that at least one physiological parameter associated with the received physiological data satisfies a physiological threshold associated with a pattern between the physiological threshold and a taggable event or a plurality of taggable events defined within an application associated with the wearable device. The operations of 910 may be performed in accordance with examples as disclosed herein. In some examples, aspects of the operations of 910 may be performed by an analysis component 630 as described with reference to FIG. 6.

At 915, the method may include identifying, based at least in part on the pattern, the taggable event or the plurality of taggable events indicating an activity the user engaged in that contributed to the at least one physiological parameter satisfying the physiological threshold. The operations of 915 may be performed in accordance with examples as disclosed herein. In some examples, aspects of the operations of 915 may be performed by an event component 635 as described with reference to FIG. 6.

At 920, the method may include causing a GUI of a device running the application to prompt the user to provide feedback associated with the identified taggable event or the identified plurality of taggable events. The operations of 920 may be performed in accordance with examples as disclosed herein. In some examples, aspects of the operations of 920 may be performed by a feedback component 640 as described with reference to FIG. 6.

At 925, the method may include receiving, via the GUI and based at least in part on prompting the user to provide the feedback, a confirmation that the identified taggable event or the identified plurality of taggable events is related to the activity the user engaged in. The operations of 925 may be performed in accordance with examples as disclosed herein. In some examples, aspects of the operations of 925 may be performed by a feedback component 640 as described with reference to FIG. 6.

Figure 10:
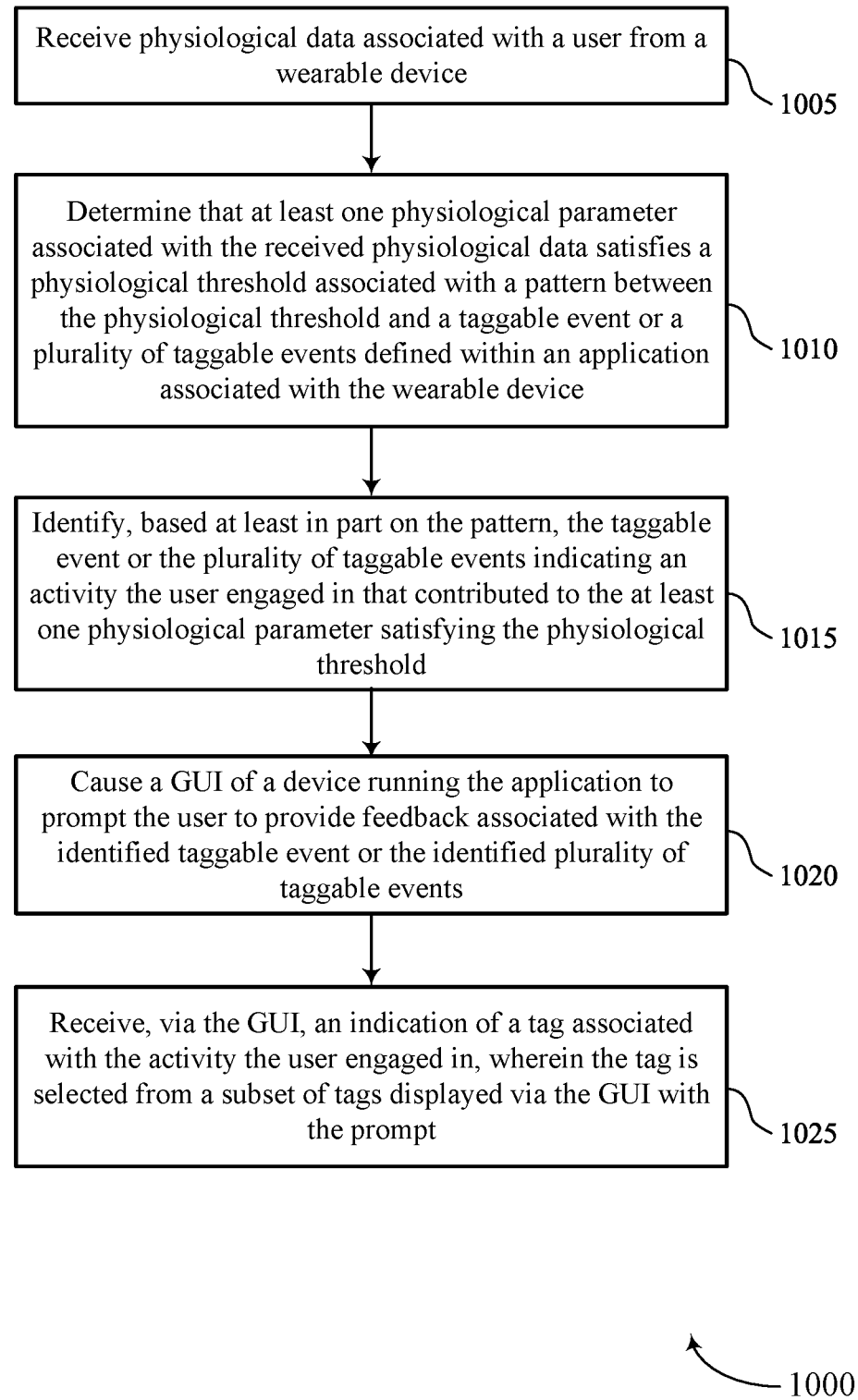

FIG. 10 shows a flowchart illustrating a method 1000 that supports techniques for providing insights according to tags and physiological data in accordance with aspects of the present disclosure. The operations of the method 1000 may be implemented by a user device or its components as described herein. For example, the operations of the method 1000 may be performed by a user device as described with reference to FIGS. 1 through 7. In some examples, a user device may execute a set of instructions to control the functional elements of the user device to perform the described functions. Additionally or alternatively, a user device may perform aspects of the described functions using special-purpose hardware.

At 1005, the method may include receiving physiological data associated with a user from a wearable device. The operations of 1005 may be performed in accordance with examples as disclosed herein. In some examples, aspects of the operations of 1005 may be performed by a data component 625 as described with reference to FIG. 6.

At 1010, the method may include determining that at least one physiological parameter associated with the received physiological data satisfies a physiological threshold associated with a pattern between the physiological threshold and a taggable event or a plurality of taggable events defined within an application associated with the wearable device. The operations of 1010 may be performed in accordance with examples as disclosed herein. In some examples, aspects of the operations of 1010 may be performed by an analysis component 630 as described with reference to FIG. 6.

At 1015, the method may include identifying, based at least in part on the pattern, the taggable event or the plurality of taggable events indicating an activity the user engaged in that contributed to the at least one physiological parameter satisfying the physiological threshold. The operations of 1015 may be performed in accordance with examples as disclosed herein. In some examples, aspects of the operations of 1015 may be performed by an event component 635 as described with reference to FIG. 6.

At 1020, the method may include causing a GUI of a device running the application to prompt the user to provide feedback associated with the identified taggable event or the identified plurality of taggable events. The operations of 1020 may be performed in accordance with examples as disclosed herein. In some examples, aspects of the operations of 1020 may be performed by a feedback component 640 as described with reference to FIG. 6.

At 1025, the method may include receiving, via the GUI, an indication of a tag associated with the activity the user engaged in, wherein the tag is selected from a subset of tags displayed via the GUI with the prompt. In some examples, the feedback includes the received tag selected from the subset of tags. The operations of 1025 may be performed in accordance with examples as disclosed herein. In some examples, aspects of the operations of 1025 may be performed by a tag component 645 as described with reference to FIG. 6.

Figure 11:
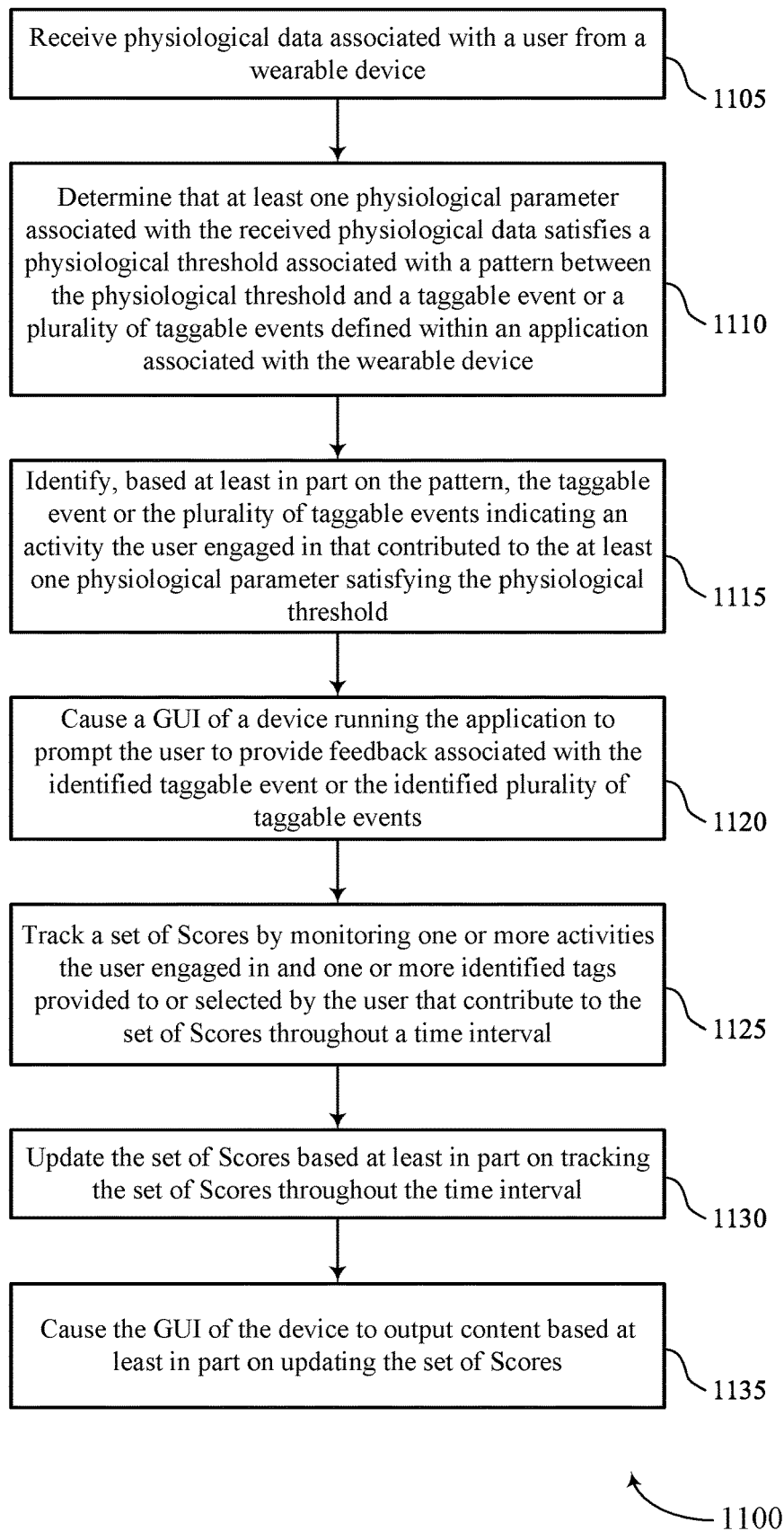

FIG. 11 shows a flowchart illustrating a method 1100 that supports techniques for providing insights according to tags and physiological data in accordance with aspects of the present disclosure. The operations of the method 1100 may be implemented by a user device or its components as described herein. For example, the operations of the method 1100 may be performed by a user device as described with reference to FIGS. 1 through 7. In some examples, a user device may execute a set of instructions to control the functional elements of the user device to perform the described functions. Additionally or alternatively, a user device may perform aspects of the described functions using special-purpose hardware.

At 1105, the method may include receiving physiological data associated with a user from a wearable device. The operations of 1105 may be performed in accordance with examples as disclosed herein. In some examples, aspects of the operations of 1105 may be performed by a data component 625 as described with reference to FIG. 6.

At 1110, the method may include determining that at least one physiological parameter associated with the received physiological data satisfies a physiological threshold associated with a pattern between the physiological threshold and a taggable event or a plurality of taggable events defined within an application associated with the wearable device. The operations of 1110 may be performed in accordance with examples as disclosed herein. In some examples, aspects of the operations of 1110 may be performed by an analysis component 630 as described with reference to FIG. 6.

At 1115, the method may include identifying, based at least in part on the pattern, the taggable event or the plurality of taggable events indicating an activity the user engaged in that contributed to the at least one physiological parameter satisfying the physiological threshold. The operations of 1115 may be performed in accordance with examples as disclosed herein. In some examples, aspects of the operations of 1115 may be performed by an event component 635 as described with reference to FIG. 6.

At 1120, the method may include causing a GUI of a device running the application to prompt the user to provide feedback associated with the identified taggable event or the identified plurality of taggable events. The operations of 1120 may be performed in accordance with examples as disclosed herein. In some examples, aspects of the operations of 1120 may be performed by a feedback component 640 as described with reference to FIG. 6.

At 1125, the method may include tracking a set of Scores by monitoring one or more activities the user engaged in and one or more identified tags provided to or selected by the user that contribute to the set of Scores throughout a time interval. The operations of 1125 may be performed in accordance with examples as disclosed herein. In some examples, aspects of the operations of 1125 may be performed by a score component 655 as described with reference to FIG. 6.

At 1130, the method may include updating the set of Scores based at least in part on tracking the set of Scores throughout the time interval. The operations of 1130 may be performed in accordance with examples as disclosed herein. In some examples, aspects of the operations of 1130 may be performed by a score component 655 as described with reference to FIG. 6.

At 1135, the method may include causing the GUI of the device to output content based at least in part on updating the set of Scores. The operations of 1135 may be performed in accordance with examples as disclosed herein. In some examples, aspects of the operations of 1135 may be performed by a score component 655 as described with reference to FIG. 6.

Figure 12:
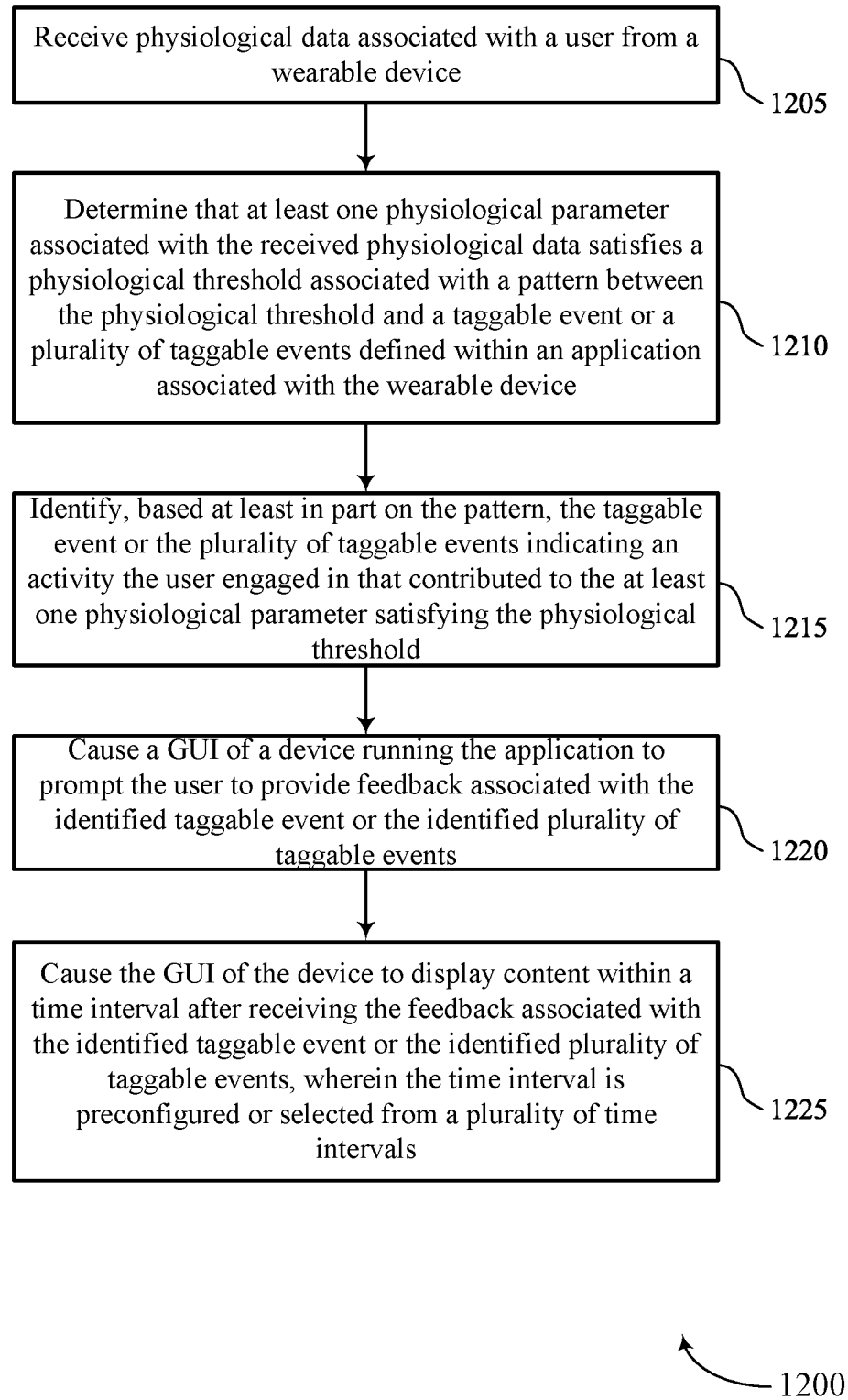

FIG. 12 shows a flowchart illustrating a method 1200 that supports techniques for providing insights according to tags and physiological data in accordance with aspects of the present disclosure. The operations of the method 1200 may be implemented by a user device or its components as described herein. For example, the operations of the method 1200 may be performed by a user device as described with reference to FIGS. 1 through 7. In some examples, a user device may execute a set of instructions to control the functional elements of the user device to perform the described functions. Additionally or alternatively, a user device may perform aspects of the described functions using special-purpose hardware.

At 1205, the method may include receiving physiological data associated with a user from a wearable device. The operations of 1205 may be performed in accordance with examples as disclosed herein. In some examples, aspects of the operations of 1205 may be performed by a data component 625 as described with reference to FIG. 6.

At 1210, the method may include determining that at least one physiological parameter associated with the received physiological data satisfies a physiological threshold associated with a pattern between the physiological threshold and a taggable event or a plurality of taggable events defined within an application associated with the wearable device. The operations of 1210 may be performed in accordance with examples as disclosed herein. In some examples, aspects of the operations of 1210 may be performed by an analysis component 630 as described with reference to FIG. 6.

At 1215, the method may include identifying, based at least in part on the pattern, the taggable event or the plurality of taggable events indicating an activity the user engaged in that contributed to the at least one physiological parameter satisfying the physiological threshold. The operations of 1215 may be performed in accordance with examples as disclosed herein. In some examples, aspects of the operations of 1215 may be performed by an event component 635 as described with reference to FIG. 6.

At 1220, the method may include causing a GUI of a device running the application to prompt the user to provide feedback associated with the identified taggable event or the identified plurality of taggable events. The operations of 1220 may be performed in accordance with examples as disclosed herein. In some examples, aspects of the operations of 1220 may be performed by a feedback component 640 as described with reference to FIG. 6.

At 1225, the method may include causing the GUI of the device to display content within a time interval after receiving the feedback associated with the identified taggable event or the identified plurality of taggable events, wherein the time interval is preconfigured or selected from a plurality of time intervals. The operations of 1225 may be performed in accordance with examples as disclosed herein. In some examples, aspects of the operations of 1225 may be performed by a content component 660 as described with reference to FIG. 6.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A method for physiological pattern recognition, comprising:

receiving physiological data associated with a user from a wearable device;

determining that at least one physiological parameter associated with the received physiological data satisfies a physiological threshold associated with a pattern between the physiological threshold and a subset of taggable event types of a plurality of taggable event types defined within an application associated with the wearable device;

determining that a temporal difference between a plurality of first timestamps associated with the at least one physiological parameter satisfying the physiological threshold and a plurality of second timestamps associated with a received tag satisfies a temporal threshold, wherein the received tag is selected by the user from a plurality of tags, and wherein the pattern is associated with the temporal difference;

identifying, based at least on the pattern, the subset of taggable event types of the plurality of taggable event types indicating an activity in which the user engaged that contributed to the at least one physiological parameter satisfying the physiological threshold; and causing a graphical user interface of a device running the application to prompt the user to provide feedback associated with the identified subset of taggable event types of the plurality of taggable event types.

2. The method of claim 1, further comprising:

receiving, via the graphical user interface and based at least in part on prompting the user to provide the feedback, a confirmation that the identified subset of taggable event types of the plurality of taggable event types is related to the activity in which the user engaged.

3. The method of claim 1, further comprising:

receiving, via the graphical user interface, an indication of a tag associated with the activity in which the user engaged, wherein the tag is selected from a subset of tags displayed via the graphical user interface with the prompt, wherein the feedback comprises the received tag selected from the subset of tags.

4. The method of claim 1, further comprising:

determining the pattern between the physiological threshold and the subset of taggable event types of the plurality of taggable event types.

5. The method of claim 4, further comprising:

determining the plurality of first timestamps and the plurality of second timestamps, wherein determining the pattern between the physiological threshold and the subset of taggable event types of the plurality of taggable event types is based at least in part on a temporal relationship between the plurality of first timestamps and the plurality of second timestamps.

6. The method of claim 4, wherein determining the pattern between the physiological threshold and the subset of taggable event types of the plurality of taggable event types comprises:

inputting one or more respective physiological parameters associated with respective physiological data collected previously from the wearable device and one or more respective tags of a plurality of tags selected previously by the user into a machine learning model.

7. The method of claim 6, wherein the machine learning model is trained to identify temporal relationships between the one or more respective physiological parameters and each respective tag of the one or more respective tags of the plurality of tags selected previously by the user.

8. The method of claim 6, further comprising:

updating the pattern between the physiological threshold and the subset of taggable event types of the plurality of taggable event types based at least in part on inputting subsequently received physiological data from the wearable device or one or more subsequently received tags associated with the activity in which the user engaged into the machine learning model.

9. The method of claim 4, further comprising:

inputting one or more respective physiological parameters associated with respective physiological data collected previously from a plurality of users and one or more respective tags of a plurality of tags selected previously by the plurality of users into a machine learning model; and determining the pattern between the physiological threshold and the subset of taggable event types of the plurality of taggable event types based at least in part on inputting the one or more respective physiological parameters and the one or more respective tags of the plurality of tags selected previously by the plurality of users into the machine learning model.

10. The method of claim 4, further comprising:

determining a baseline value of the at least one physiological parameter associated with the received physiological data, wherein determining the pattern between the physiological threshold and the subset of taggable event types of the plurality of taggable event types is based at least in part on determining the baseline value of the at least one physiological parameter associated with the received physiological data.

11. The method of claim 1, further comprising:

causing the graphical user interface of the device running the application to provide to the user an insight identifying a relationship between the activity in which the user engaged and a metric associated with the user based at least in part on the identified subset of taggable event types of the plurality of taggable event types.

12. The method of claim 11, wherein the relationship further comprises activity information indicating a type of the activity the user engaged in, timing information indicating a timestamp of the activity the user engaged in, location information indicating a locality of the activity the user engaged in, or any combination thereof that contributed to the metric associated with the user, and wherein the insight further comprises a recommendation for adjusting the metric associated with the user.

13. The method of claim 1, further comprising:

tracking a set of Scores by monitoring one or more activities in which the user engaged and one or more identified tags provided to or selected by the user that contribute to the set of Scores throughout a time interval;

updating the set of Scores based at least in part on tracking a Readiness Score throughout the time interval; and causing the graphical user interface of the device to output content based at least in part on updating the set of Scores.

14. The method of claim 1, further comprising:

causing the graphical user interface of the device to display content within a time interval after receiving the feedback associated with the identified subset of taggable event types of the plurality of taggable event types, wherein the time interval is preconfigured or selected from a plurality of time intervals.

15. The method of claim 1, wherein the at least one physiological parameter associated with the received physiological data comprises heart rate data associated with the user, heart rate variability data associated with the user, temperature data associated with the user, respiratory rate data associated with the user, blood oxygen data associated with the user, sleep data associated with the user, activity data associated with the user, or any combination thereof.

16. The method of claim 1, wherein the wearable device comprises a wearable ring device.

17. An apparatus for physiological pattern recognition, comprising:

a processor;

memory coupled with the processor; and instructions stored in the memory and executable by the processor to cause the apparatus to:

receive physiological data associated with a user from a wearable device;

determine that at least one physiological parameter associated with the received physiological data satisfies a physiological threshold associated with a pattern between the physiological threshold and a subset of taggable event types of a plurality of taggable event types defined within an application associated with the wearable device, the subset of taggable event types comprising a set of candidate taggable events that cause the physiological parameter to satisfy the physiological threshold in accordance with the pattern;

determine that a temporal difference between a plurality of first timestamps associated with the at least one physiological parameter satisfying the physiological threshold and a plurality of second timestamps associated with a received tag satisfies a temporal threshold, wherein the received tag is selected by the user from a plurality of tags, and wherein the pattern is associated with the temporal difference;

identify, based at least in part on the pattern, the subset of taggable event types of the plurality of taggable event types indicating an activity the user engaged in that contributed to the at least one physiological parameter satisfying the physiological threshold; and cause a graphical user interface of a device running the application to display the set of candidate taggable events and to prompt the user to indicate whether the set of candidate taggable events caused the physiological parameter to satisfy the physiological threshold.

18. The apparatus of claim 17, wherein the instructions are further executable by the processor to cause the apparatus to:

receive, via the graphical user interface and based at least in part on prompting the user, a confirmation that the set of candidate taggable events caused the physiological parameter to satisfy the physiological threshold.

19. A non-transitory computer-readable medium storing code for physiological pattern recognition, the code comprising instructions executable by a processor to:

receive physiological data associated with a user from a wearable device;

determine that at least one physiological parameter associated with the received physiological data satisfies a physiological threshold associated with a pattern between the physiological threshold and a subset of taggable event types of a plurality of taggable event types defined within an application associated with the wearable device;

determine that a temporal difference between a plurality of first timestamps associated with the at least one physiological parameter satisfying the physiological threshold and a plurality of second timestamps associated with a received tag satisfies a temporal threshold, wherein the received tag is selected by the user from a plurality of tags, and wherein the pattern is associated with the temporal difference;

identify, based at least in part on the pattern, the subset of taggable event types of the plurality of taggable event types indicating an activity the user engaged in that contributed to the at least one physiological parameter satisfying the physiological threshold; and cause a graphical user interface of a device running the application to prompt the user to provide feedback associated with the identified subset of taggable event types of the plurality of taggable event types.

* * * * *